United States Patent [19]

Yamaguchi et al.

[11] Patent Number: 4,816,063
[45] Date of Patent: Mar. 28, 1989

[54] THIADIAZABICYCLONONANE DERIVATIVES, PROCESSES FOR THEIR PRODUCTION AND HERBICIDAL COMPOSITIONS

[75] Inventors: Mikio Yamaguchi, Shimada; Yukihiro Watase, Shizuoka; Takeshi Kambe, Tokyo; Susumu Katou, Shizuoka, all of Japan

[73] Assignees: Kumiai Chemical Industry Co., Ltd.; Ihara Chemical Industry Co., Ltd., both of Tokyo, Japan

[21] Appl. No.: 910,978

[22] Filed: Sep. 24, 1986

[30] Foreign Application Priority Data

Mar. 25, 1986 [JP] Japan .................................. 61-66567

[51] Int. Cl.$^4$ .................... C07D 513/04; A01N 43/82
[52] U.S. Cl. ............................................... 71/90; 71/87; 544/232; 544/235; 544/224; 544/238
[58] Field of Search ...................... 71/87, 90; 544/232, 544/235

[56] References Cited

U.S. PATENT DOCUMENTS 3,726,891  4/1973  Pilgram et al. ...................... 71/90

FOREIGN PATENT DOCUMENTS 1039442  8/1966  United Kingdom .................... 71/90

OTHER PUBLICATIONS

Wakabayashi et al. in *Advances in Pesticide Science* (H. Geissbühler, Editor) pp. 256–260 (1978).
Patent Abstracts of Japan, vol. 8, No. 85(C-219) [1522], Apr. 18, 1984; for JP-A-59 7180 (Fujisawa Yakuhin K.K.).
S. W. Moje et al.: *Journal of Organic Chemistry*, vol. 39, No. 20, 1974, pp. 2951–1956, "Syntheses and Reactions of 3,4-Dialkyl-1, 3, 4-Thiadiazolidine -2, 5-Diones".
Patent Abstracts of Japan, vol. 8, No. 130, Jun. 16, 1984 (C-229) [1567]; for JP-A-59 42384 (Nippon Kayaku K. K.).
Chemical Abstracts, vol. 107, No. 15, Oct. 12, 1987, p. 725, Abstract No. 134316u, for JP 6200091.

*Primary Examiner*—Donald G. Daus
*Assistant Examiner*—E. Bernhardt
*Attorney, Agent, or Firm*—Oblon, Fisher, Spivak, McClelland & Maier

[57] ABSTRACT

As a herbicide 9-phenylimino-8-thia-1,6-diazabicyclo[4.3.0]nonane-7-(one or thione) compound having the formula:

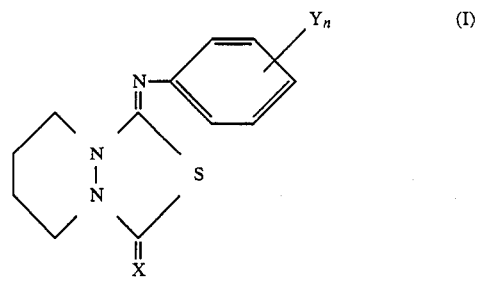

wherein Y represents halogen, hydroxyl, alkyl, alkoxy which may be substituted by halogen, alkenyloxy, alkynyloxy, phenoxy, cycloalkyloxy, alkoxycarbonylalkyloxy alkoxycarbonylalkenyloxy, alkythiocarbonylalkyloxy, alkynyloxycarbonylalkyloxy, benzyloxycarbonylalkyloxy, trifluoromethyl, benzyloxy, alkenyl, cyanoalkyl, alkylcarbamoyloxy, benzyl, alkoxyalkyl, alkynyloxyalkyl, cycloalkylmethyloxy, alkoxyalkyloxy, phenethyloxy, cycloalkyloxycarbonylalkyloxy, pyrrolidinocarbonyl, phenylcarbonyl,

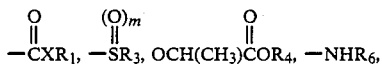

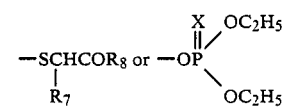

n is an integer of from 0 to 3; and X is oxygen or sulfur.

12 Claims, 25 Drawing Sheets

THIADIAZABICYCLONONANE DERIVATIVES, PROCESSES FOR THEIR PRODUCTION AND HERBICIDAL COMPOSITIONS

The present invention relates to novel 9-phenylimino-8-thia-1,6-diazabicyclo[4.3.0]nonane-7-(one or thione) derivatives, processes for their production and herbicidal compositions containing them.

In recent years, a number of herbicides have been developed and actually used, and they have contributed to the reduction of the agricultural work load and to the improvement of the productivity. As a herbicide having a hetero ring, Ronstar [i.e. 5-t-butyl-3-(2,4-dichloro-5-isopropoxyphenyl)-1,3,4-oxadiazoline-2-one] is widely used. However, Ronstar has drawbacks that it is likely to bring about phytotoxicity, and it is not effective against perennial weeds, particularly against Sagitaria pygmaea. Accordingly, a development of a herbicide having improved effectiveness and safety has been desired.

Under the circumstances, the present inventors have conducted extensive researches with an aim to develop a herbicide which satisfies the following conditions, and have finally accomplished the present invention.

(1) It is effective at a low dose.

(2) It is effective against paddy field weeds and (or) against upland field weeds.

(3) It is also effective against perennial weeds.

(4) It is effective in a wide range covering the germination stage to the growing stage.

(5) It has excellent residual effects and can be expected to provide stabilized effects.

(6) It exhibits excellent herbicidal effects.

(7) It is highly safe to crop plants.

Thus, the present invention provides a 9-phenylimino-8-thia-1,6-diazabicyclo[4.3.0]nonane-7-(one or thione) derivative having the formula:

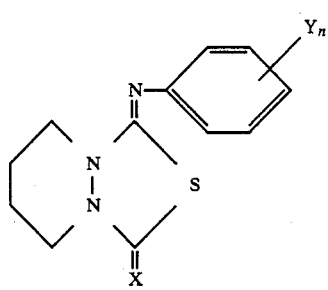

wherein Y which may be the same or different, represents halogen, hydroxy, alkyl, alkoxy which may be substituted by halogen, alkenyloxy which may be substituted by halogen, alkynyloxy, phenoxy, cycloalkyloxy, alkoxycarbonylalkyloxy, alkoxycarbonylalkenyloxy, alkylthiocarbonylalkyloxy, alkynyloxycarbonylalkyloxy, benzyloxycarbonylalkyloxy, trifluoromethyl, benzyloxy which may be substituted by chlorine or alkyl, alkenyl, cyanoalkyl, alkylcarbamoyloxy, benzyl which may be substituted by one or two alkyl, alkoxyalkyl, alkynyloxyalkyl, cycloalkylmethyloxy which may be substituted by halogen, alkoxyalkyloxy, phenethyloxy, cycloalkyloxycarbonylalkyloxy, pyrrolidinocarbonyl, phenylcarbonyl which may be substituted by alkyl,

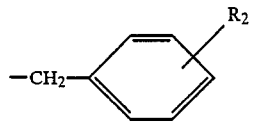

[wherein $R_1$ is hydrogen, alkyl, phenyl, cycloalkyl, alkoxyalkyl, alkoxycarbonylalkyl or

(wherein $R_2$ is hydrogen or alkoxy), X is oxygen or sulfur],

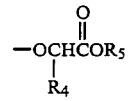

(wherein $R_3$ is alkyl, alkenyl or alkynyl, and m is 0 or 2),

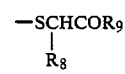

[wherein $R_4$ is hydrogen or alkyl, and $R_5$ is hydrogen, alkyl, alkoxyalkyl, tetrahydrofurfuryl, alkoxyalkyloxyalkyl, alkoxycarbonylalkyl, cycloalkyl or —N=C(CH$_3$)—$R_6$ (wherein $R_6$ is alkyl or phenyl)], —NHR$_7$ (wherein $R_7$ is alkylcarbonyl or alkoxycarbonylalkyl),

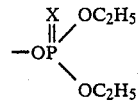

(wherein $R_8$ is hydrogen or alkyl, and $R_9$ is alkoxy, cycloalkyloxy or 1-pyrrolidinyl), or $$-OP\begin{matrix}X\\\|\end{matrix}\begin{matrix}OC_2H_5\\OC_2H_5\end{matrix}$$

(wherein X is as defined above); n is an integer of from 0 to 3; and X is oxygen or sulfur.

The present invention also provides a process for producing a 9-phenylimino-8-thia-1,6-diazabicyclo[4.3.0]nonane-7-(one or thione) derivative having the formula:

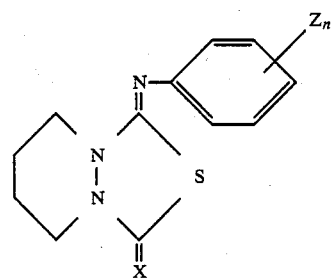

wherein Z which may be the same or different, represents halogen, alkyl, alkoxy which may be substituted by halogen, alkenyloxy which may be substituted by halogen, alkynyloxy, phenoxy, cycloalkyloxy, alkoxycarbonylalkyloxy, alkylthiocarbonylalkyloxy, alkynyloxycarbonylalkyloxy, benzyloxycarbonylalkyloxy, trifluoromethyl, benzyloxy which may be substituted by chlorine or alkyl, alkenyl, cyanoalkyl, alkylcarbamoyloxy, benzyl which may be substituted by one or two alkyl, alkoxyalkyl, alkynyloxyalkyl, cycloalkylmethyloxy, alkoxyalkyloxy, phenethyloxy, cycloalkyloxycarbonylalkyloxy, pyrrolidinocarbonyl, phenylcarbonyl which may be substituted by alkyl,

[wherein $R_1$ is hydrogen, alkyl, phenyl, cycloalkyl, alkoxyalkyl, alkoxycarbonylalkyl or

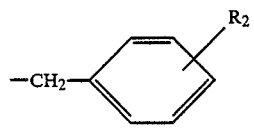

(wherein $R_2$ is hydrogen or alkoxy), X is oxygen or sulfur],

(wherein $R_3$ is alkyl, alkenyl or alkynyl, and m is 0 or 2),

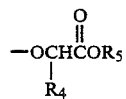

[wherein $R_4$ is hydrogen or alkyl, and $R_5$ is hydrogen, alkyl, alkoxyalkyl, tetrahydrofurfuryl, alkoxyalkyloxyalkyl, alkoxycarbonylalkyl, cycloalkyl or —N=C(CH$_3$)—R$_6$ (wherein $R_6$ is alkyl or phenyl)], —NHR$_7$ (wherein $R_7$ is alkylcarbonyl),

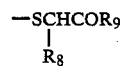

(wherein $R_8$ is hydrogen or alkyl, and $R_9$ is alkoxy, cycloalkyloxy or 1-pyrrolidinyl), or

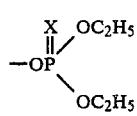

(wherein X is as defined above); n is an integer of from 0 to 3; and X is oxygen or sulfur, which comprises reacting a compound of the formula:

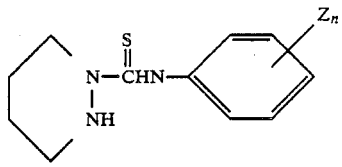

wherein Z and n are as defined above, with a compound of the formula:

CXCl$_2$ wherein X is as defined above.

Further, the present invention provides a process for producing a 9-phenylimino-8-thia-1,6-diazabicyclo[4.3.0]nonane-7-(one or thione) derivative having the formula:

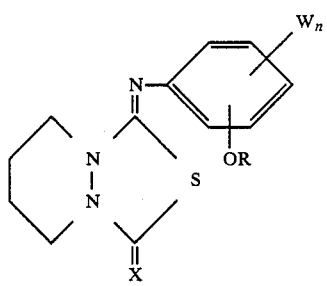

wherein W which may be the same or different, represents halogen; R is alkyl which may be substituted by halogen, alkenyl which may be substituted by halogen, alkynyl, alkoxycarbonylalkyl, alkoxycarbonylalkenyloxy, alkylthiocarbonylalkyl, alkynyloxycarbonylalkyl, benzyloxycarbonylalkyl, benzyl which may be substituted by chlorine or alkyl, alkylcarbamoyl, cycloalkylmethyl which may be substituted by halogen, phenethyl,

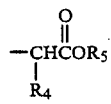

[wherein $R_4$ is hydrogen or alkyl, and $R_5$ is alkyl, alkoxyalkyl, tetrahydrofurfuryl, alkoxyalkyloxyalkyl, alkoxycarbonylalkyl, cycloalkyl or —N=C(CH$_3$)—R$_6$ (wherein $R_6$ is alkyl or phenyl)], or

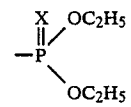

(wherein X is oxygen or sulfur); n is an integer of from 0 to 3; and X is oxygen or sulfur, which comprises reacting a compound of the formula:

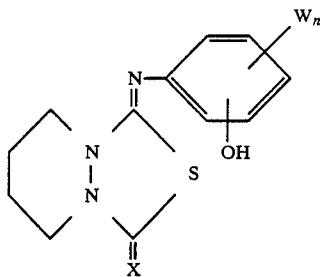

wherein W, X and n are as defined above, with a compound of the formula RT wherein R is as defined above, and T is halogen.

Furthermore, the present invention provides a herbicidal composition comprising a herbicidally effective amount of a compound of the formula I as defined above and a carrier.

Now, the present invention will be described in detail with reference to the preferred embodiments.

Figure 1:
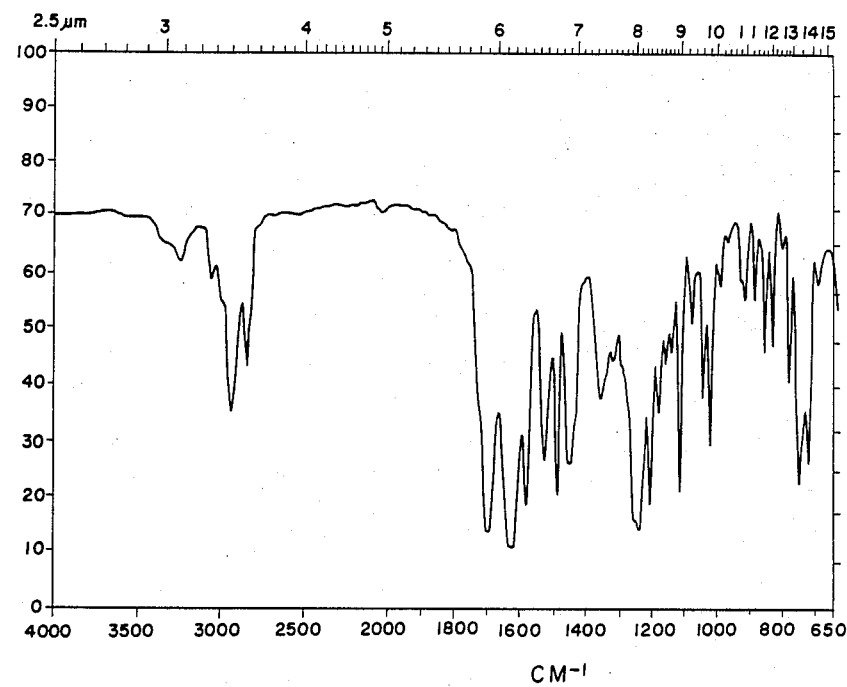
FIG. 1 is the infrared absorption spectrum of Compound No. 3.
Figure 2:
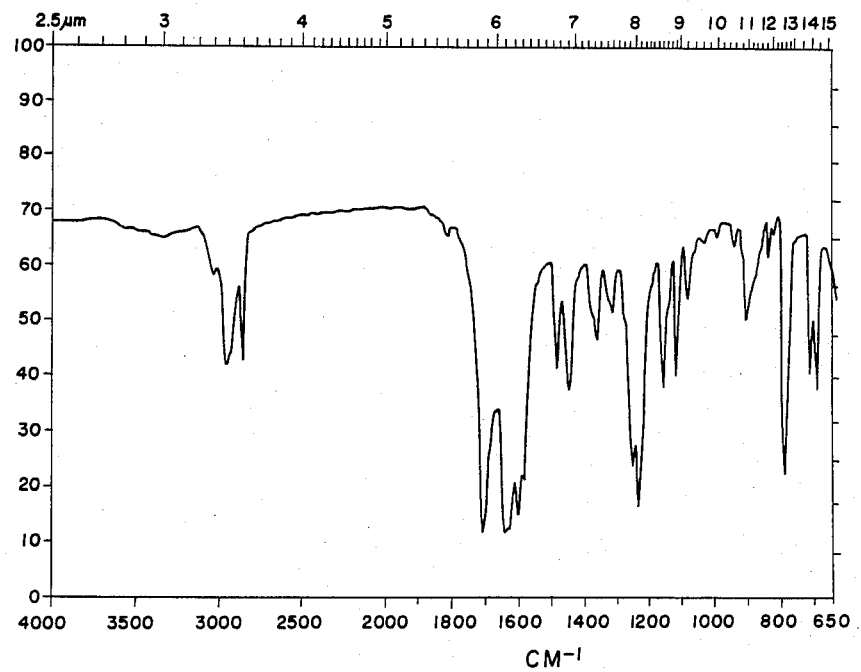
FIG. 2 is the infrared absorption spectrum of Compound No. 6.
Figure 3:
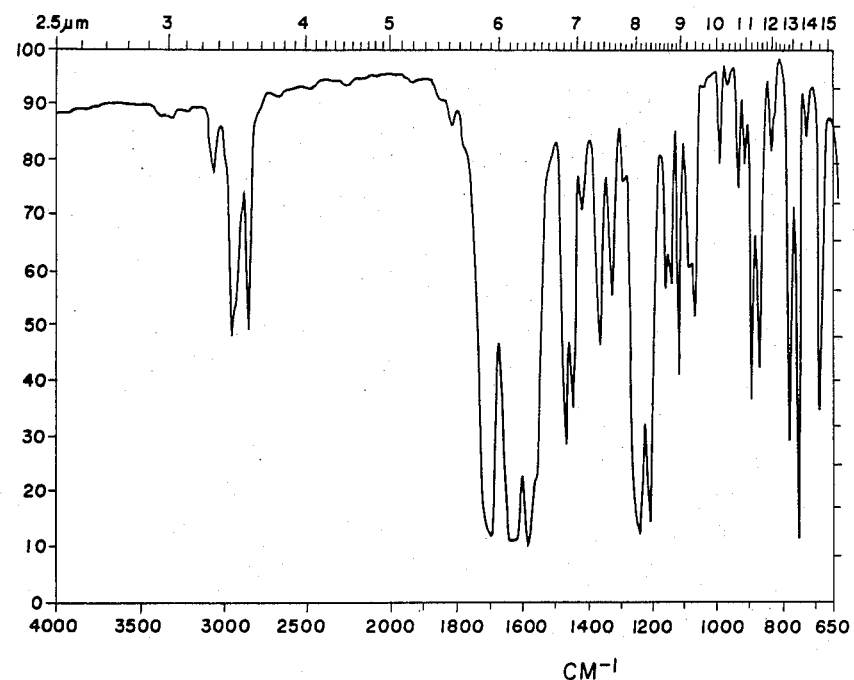
FIG. 3 is the infrared absorption spectrum of Compound No. 7.
Figure 4:
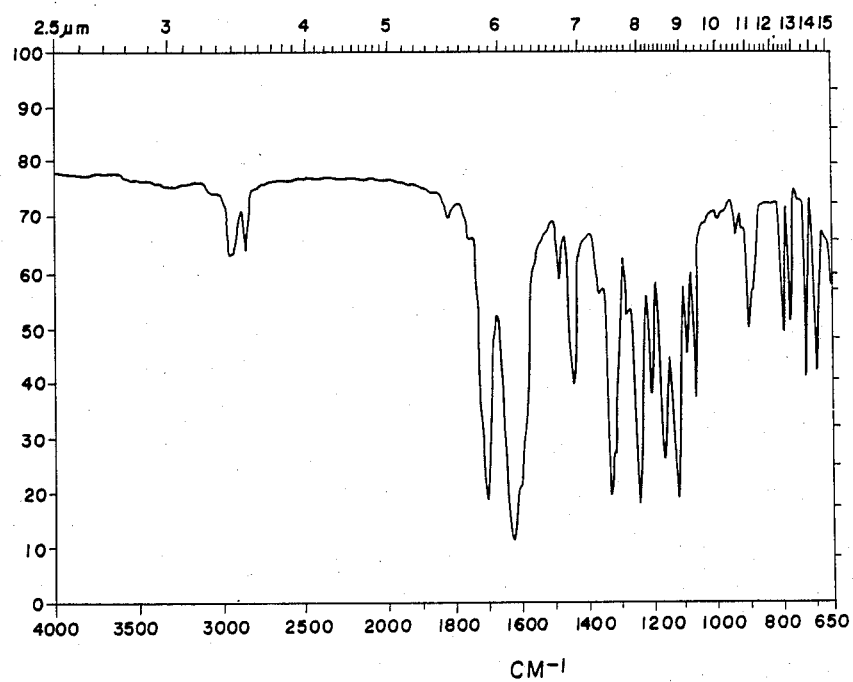
FIG. 4 is the infrared absorption spectrum of Compound No. 8.
Figure 5:
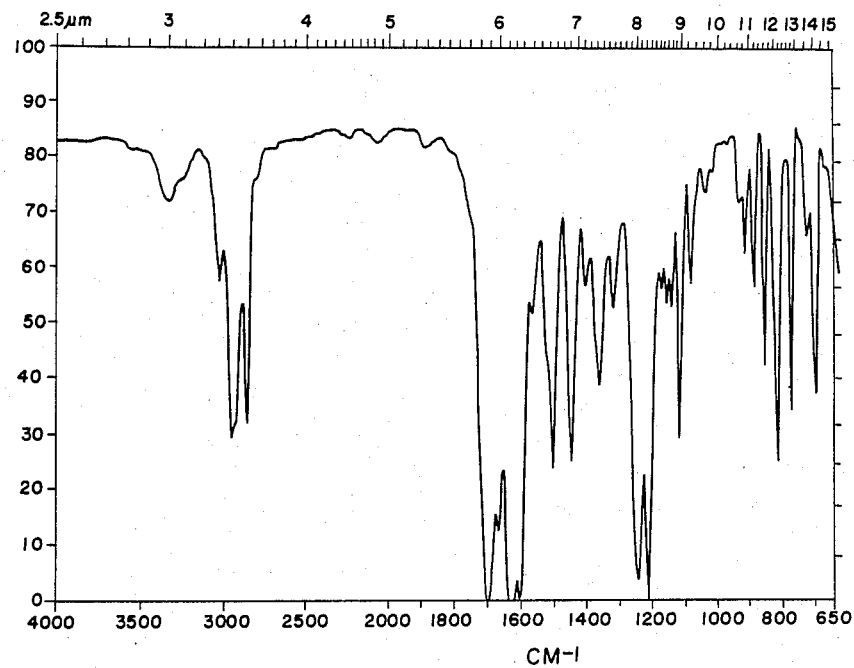
FIG. 5 is the infrared absorption spectrum of Compound No. 9.
Figure 6:
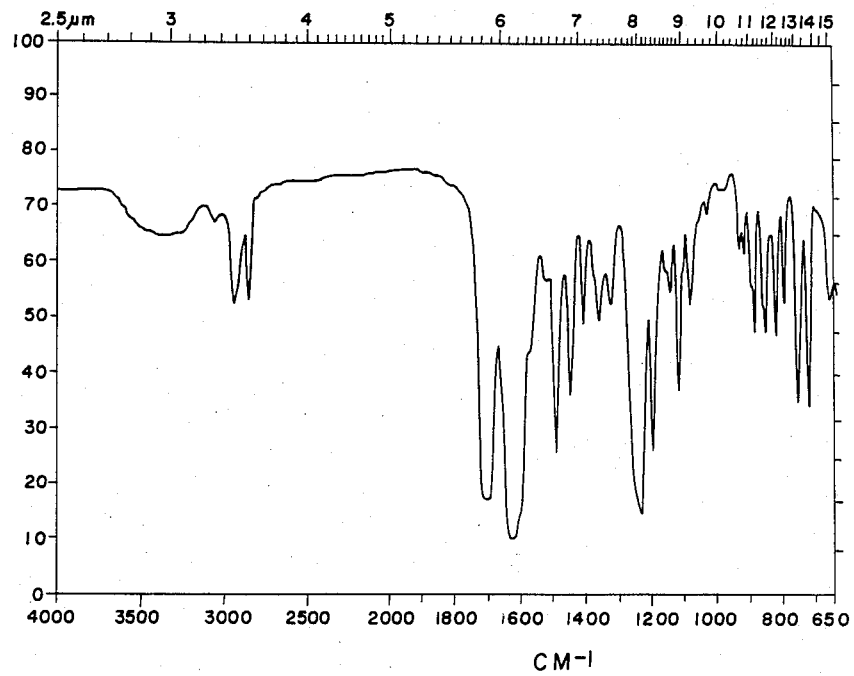
FIG. 6 is the infrared absorption spectrum of Compound No. 16.
Figure 7:
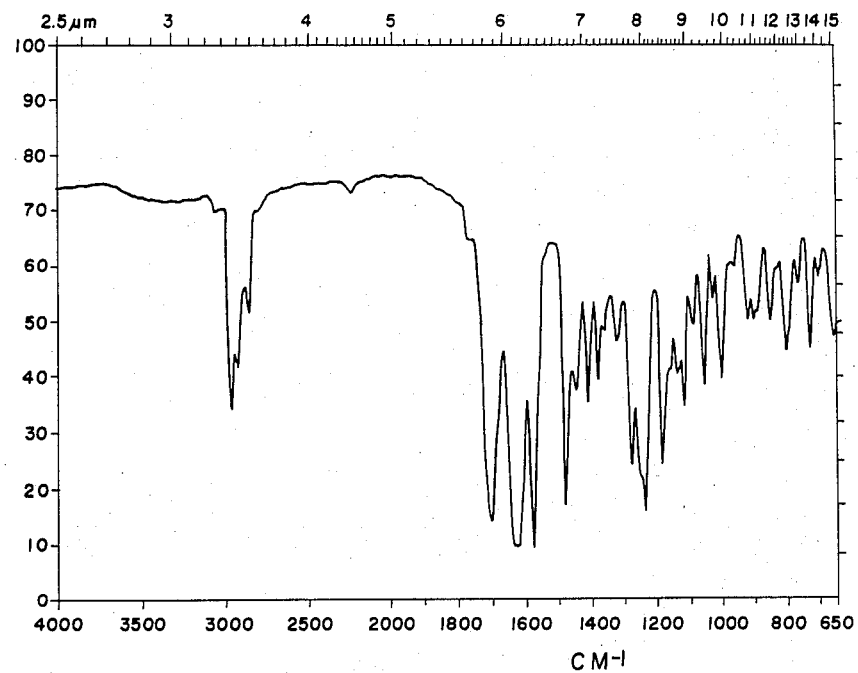
FIG. 7 is the infrared absorption spectrum of Compound No. 24.
Figure 8:
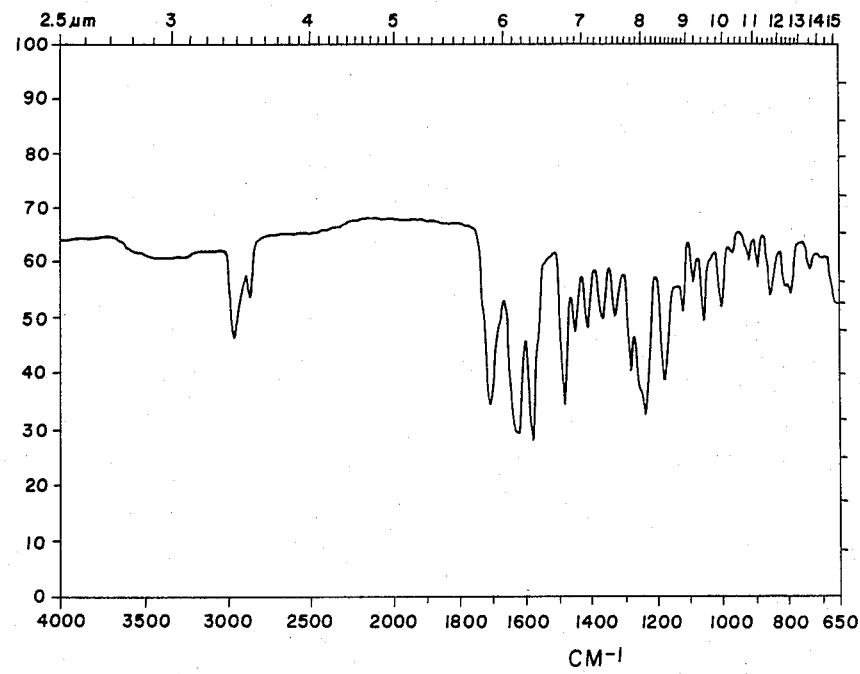
FIG. 8 is the infrared absorption spectrm of Compound No. 25.
Figure 9:
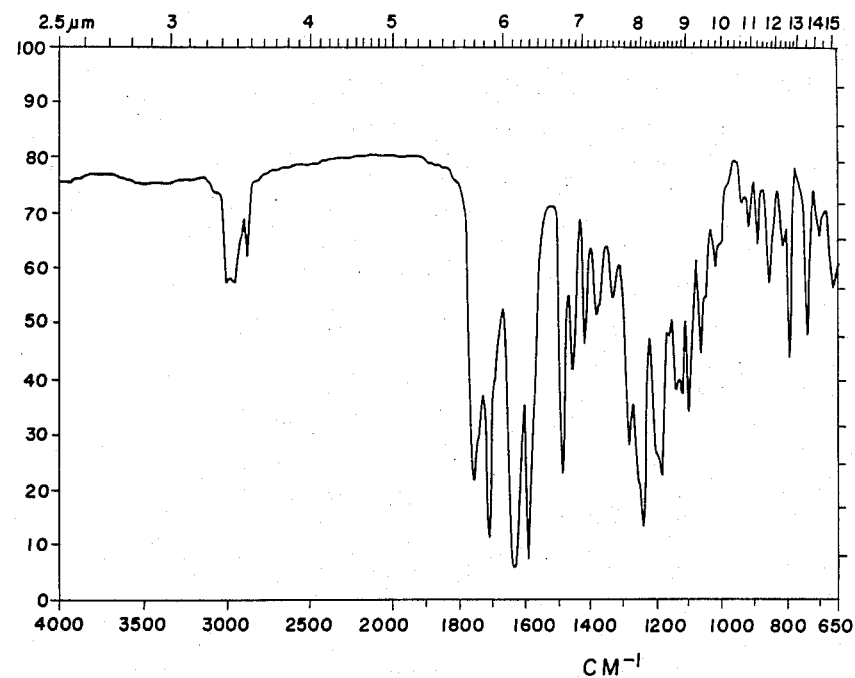
FIG. 9 is the infrared absorption spectrum of Compound No. 28.
Figure 10:
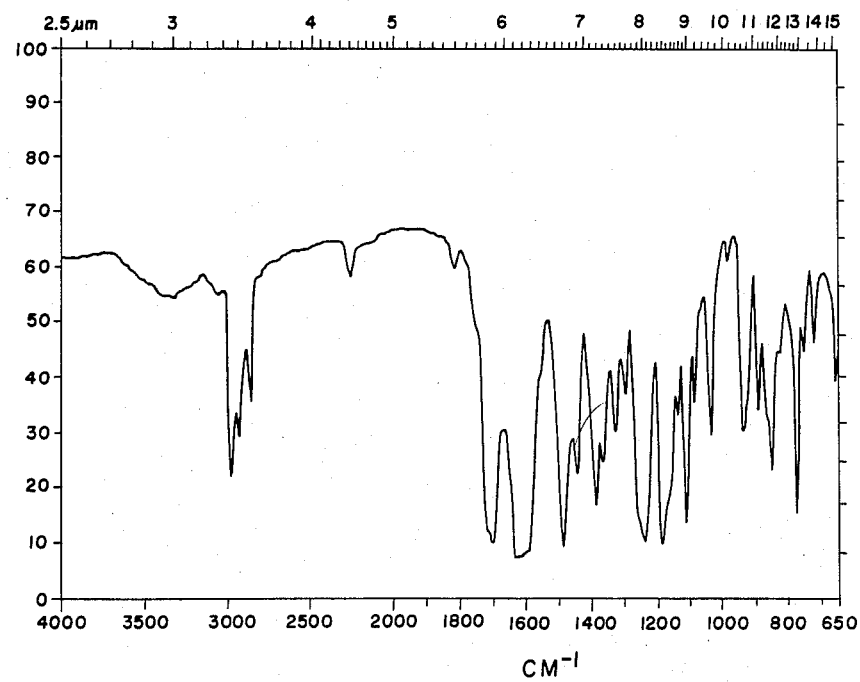
FIG. 10 is the infrared absorption spectrum of Compound No. 33.
Figure 11:
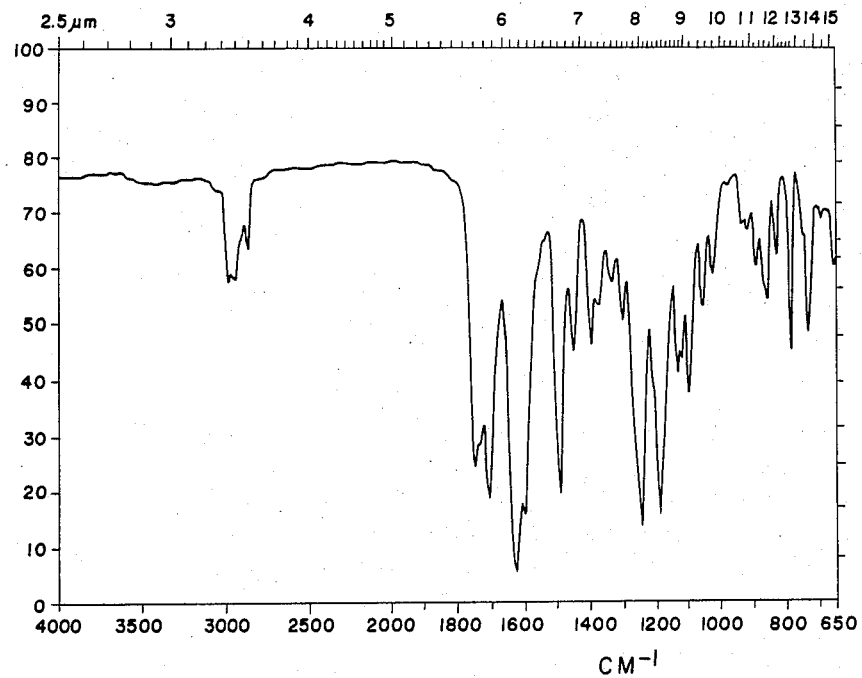
FIG. 11 is the infrared absorption spectrum of Compound No. 36.
Figure 12:
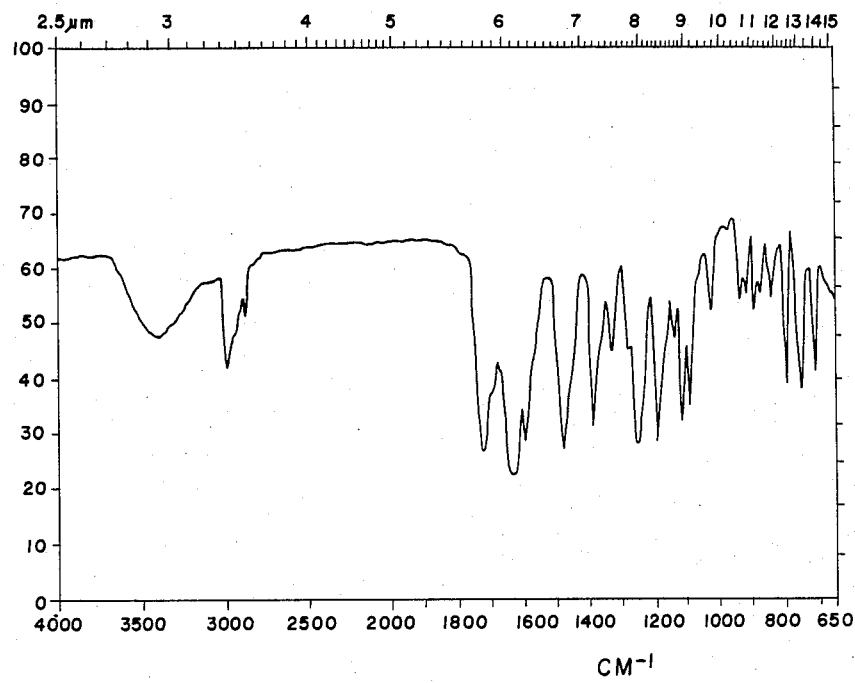
FIG. 12 is the infrared absorption spectrum of Compound No. 39.
Figure 13:
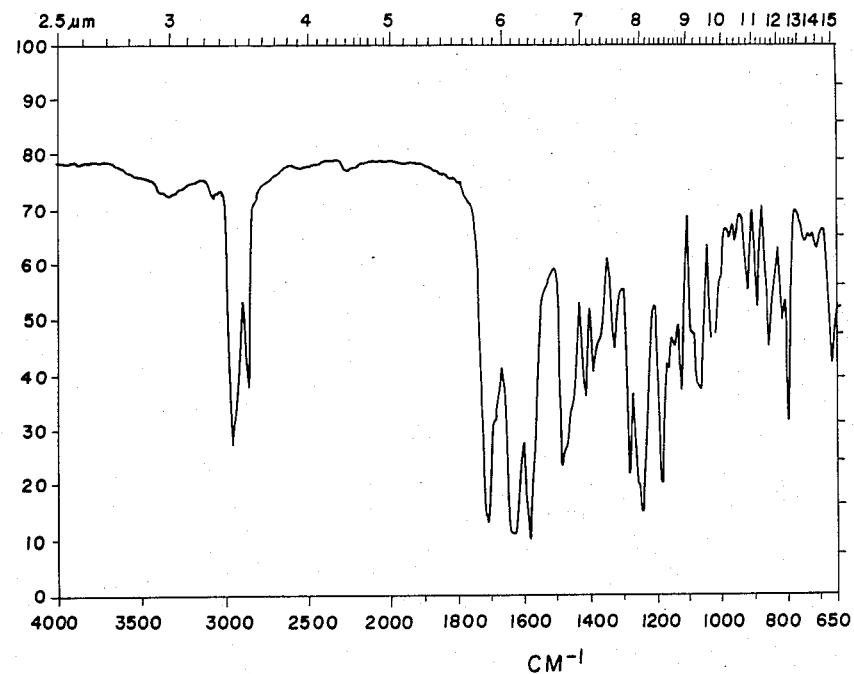
FIG. 13 is the infrared absorption spectrum of Compound No. 48.
Figure 14:
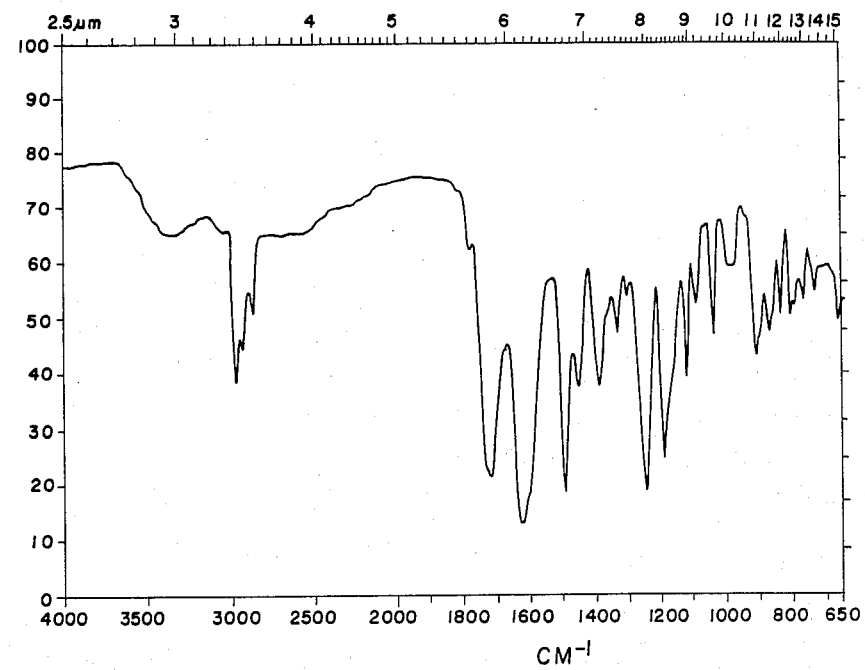
FIG. 14 is the infrared absorption spectrum of Compound No. 49.
Figure 15:
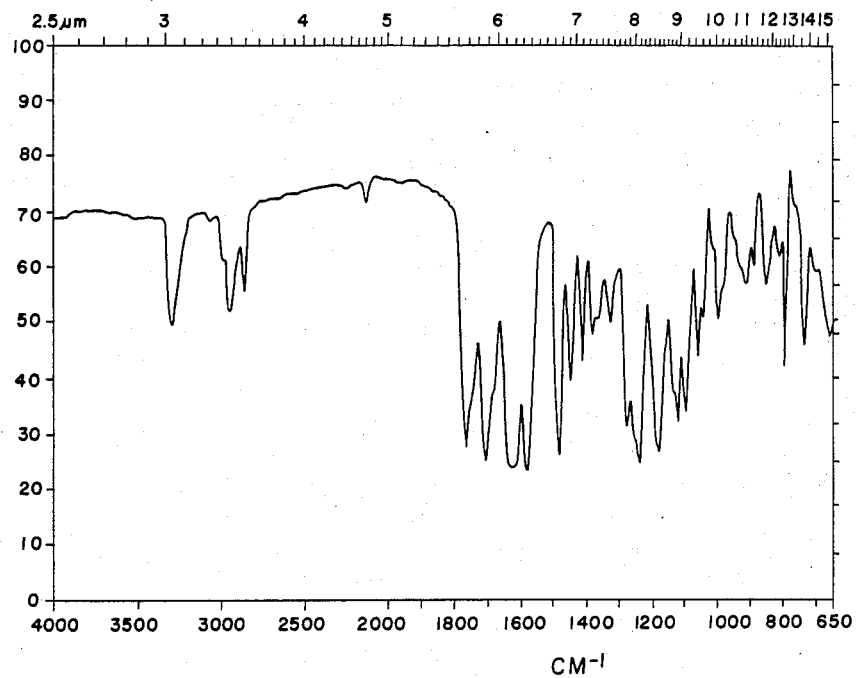
FIG. 15 is the infrared absorption spectrum of Compound No. 50.
Figure 16:
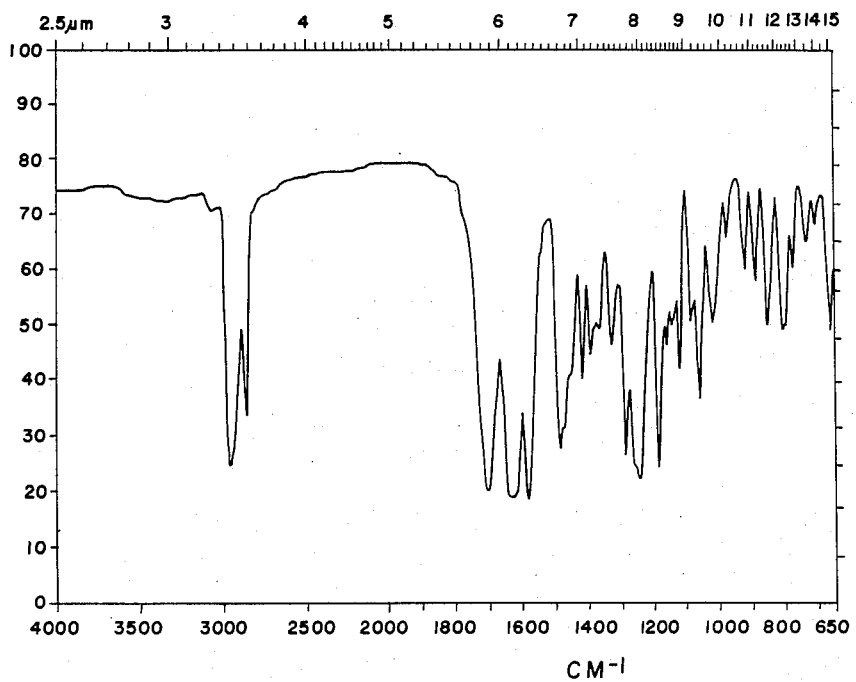
FIG. 16 is the infrared absorption spectrum of Compound No. 51.
Figure 17:
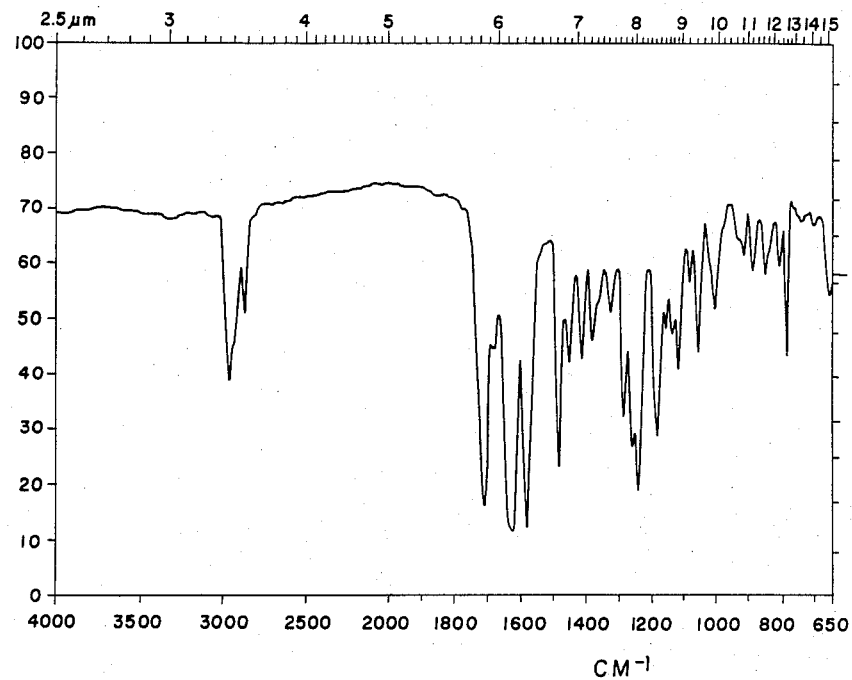
FIG. 17 is the infrared absorption spectrum of Compound No. 52.
Figure 18:
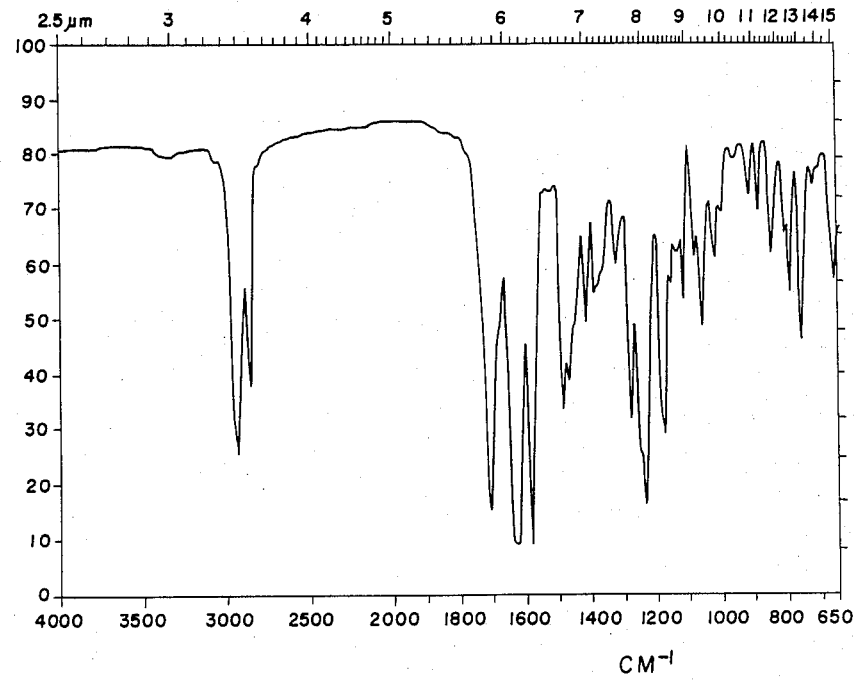
FIG. 18 is the infrared absorption spectrum of Compound No. 55.
Figure 19:
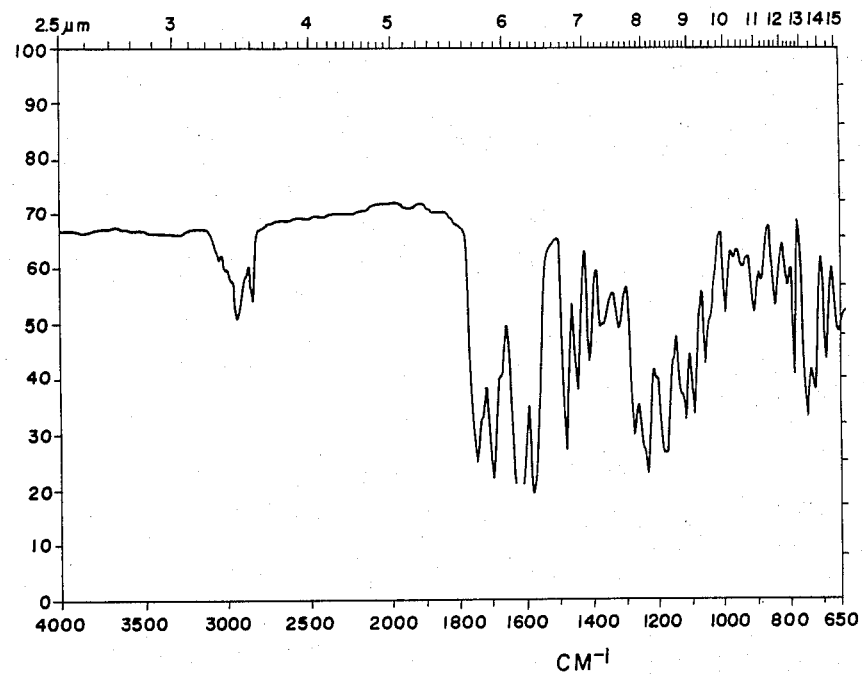
FIG. 19 is the infrared absorption spectrum of Compound No. 56.
Figure 20:
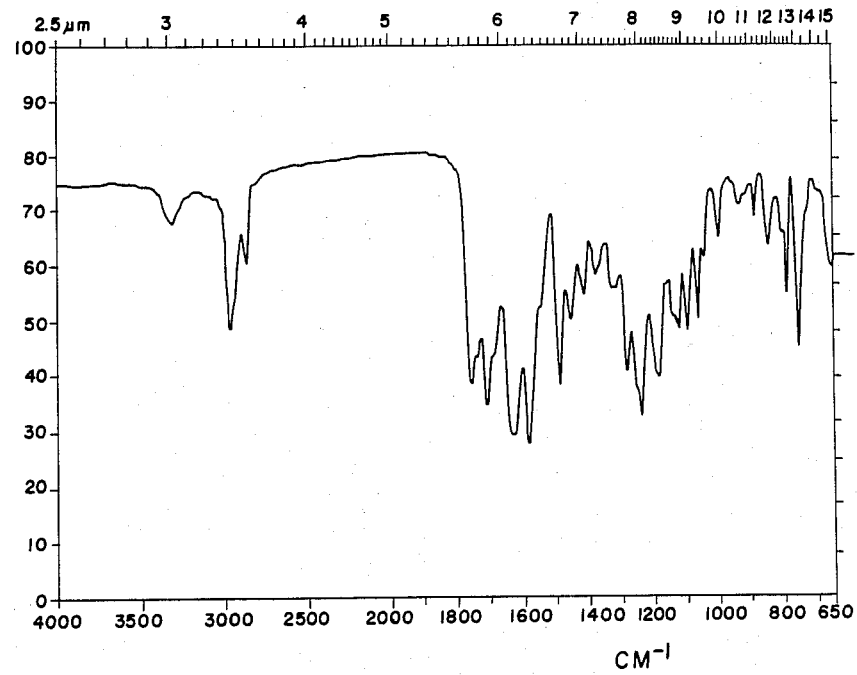
FIG. 20 is the infrared absorption spectrum of Compound No. 59.
Figure 21:
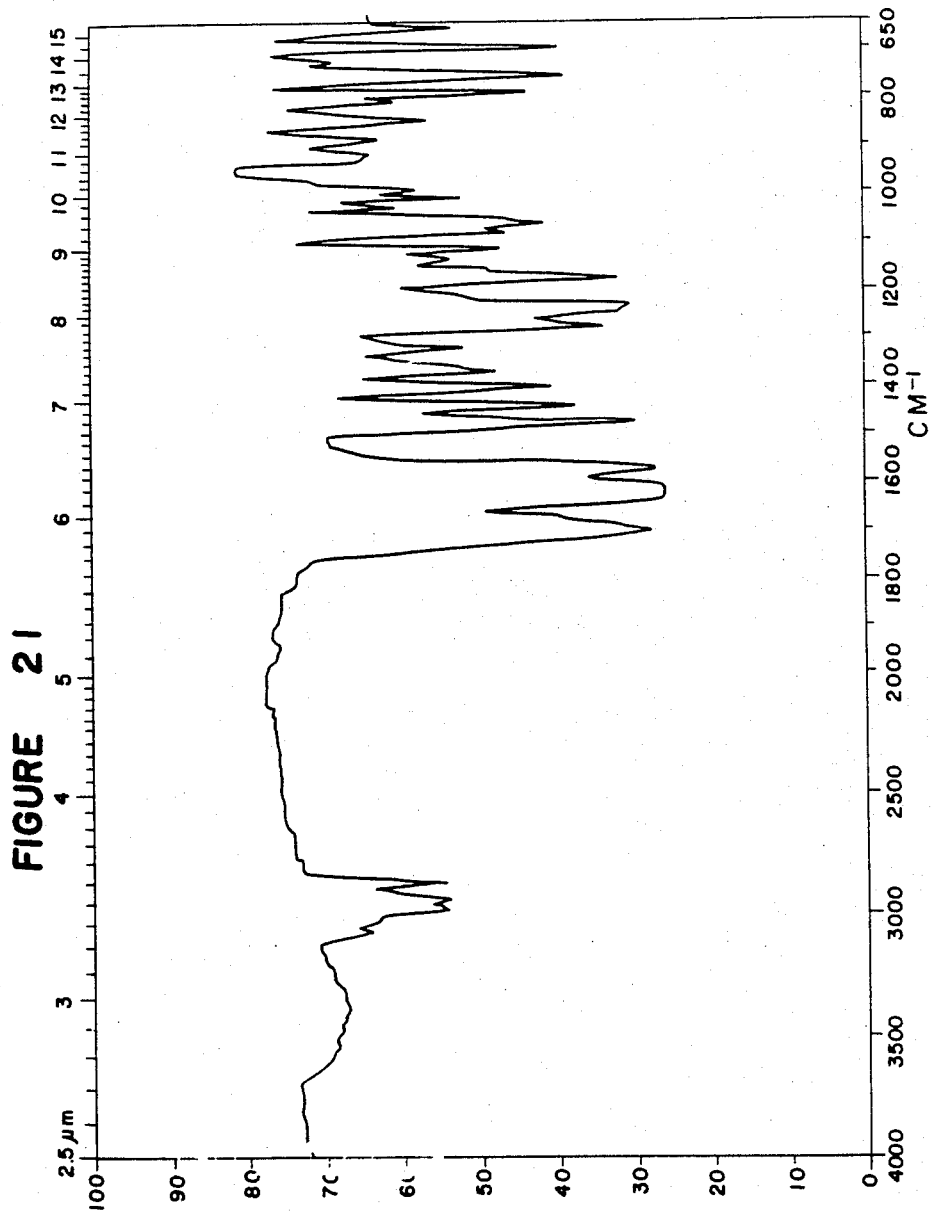
FIG. 21 is the infrared absorption spectrum of Compound No. 75.
Figure 22:
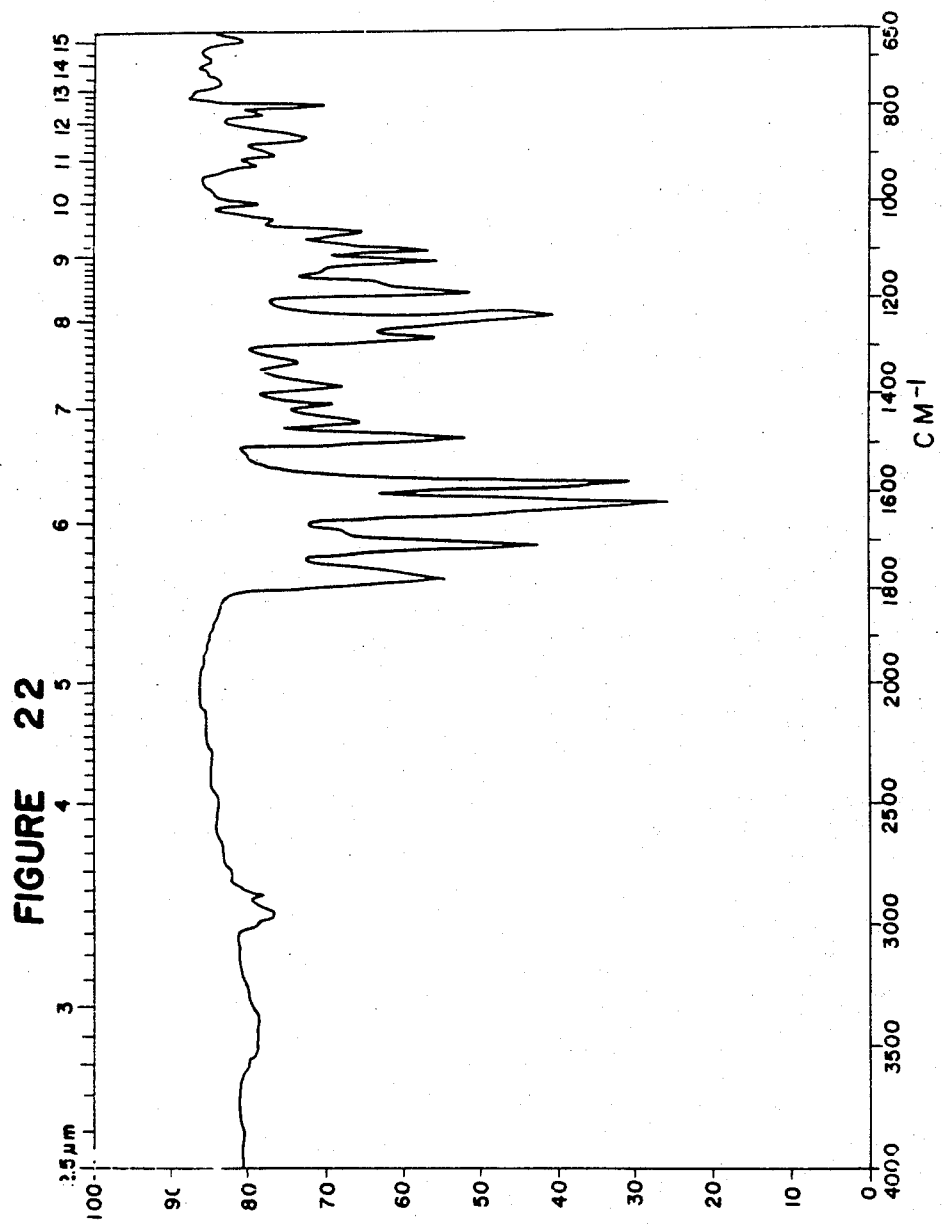
FIG. 22 is the infrared absorption spectrum of Compound No. 84.
Figure 23:
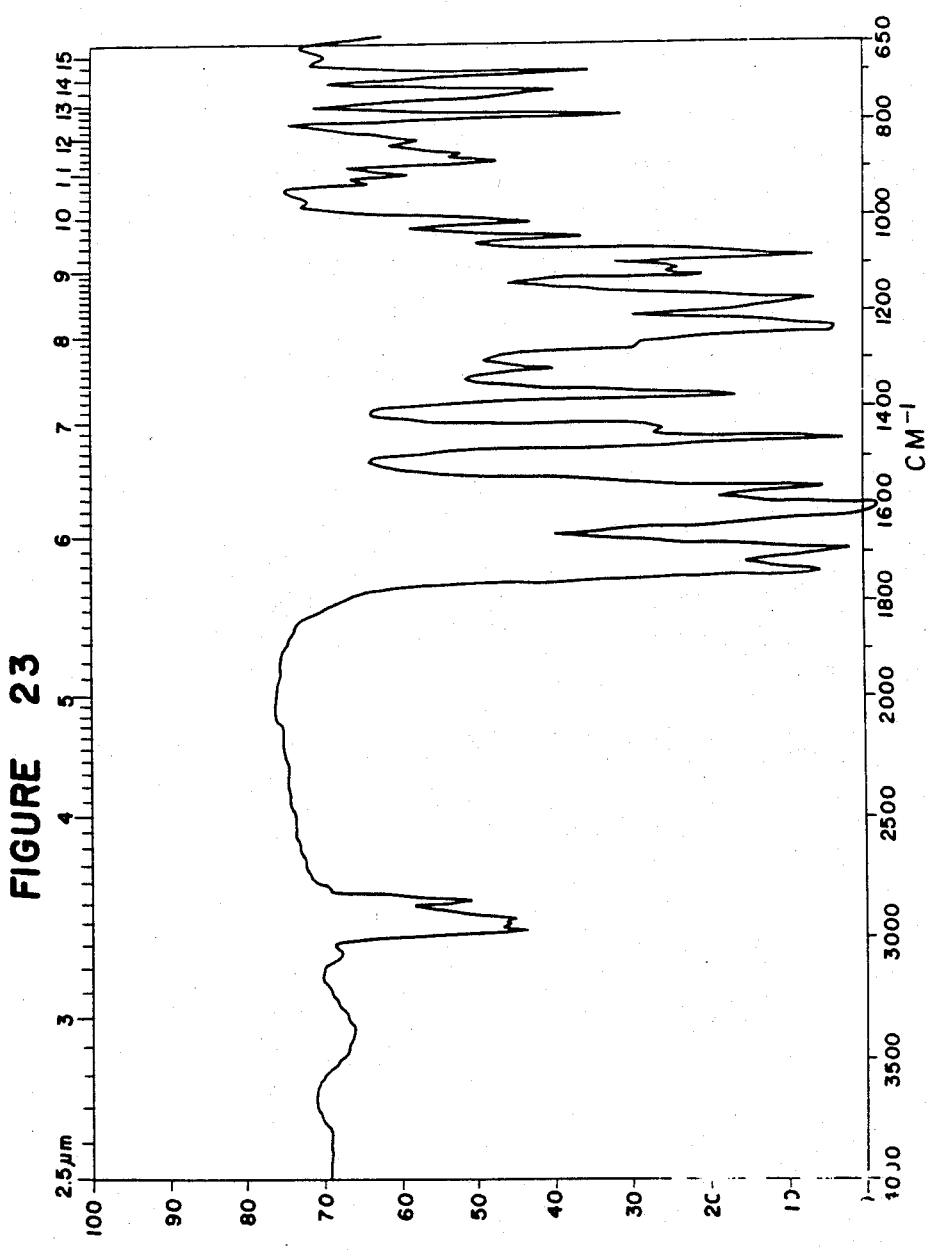
FIG. 23 is the infrared absorption spectrum of Compound No. 86.
Figure 24:
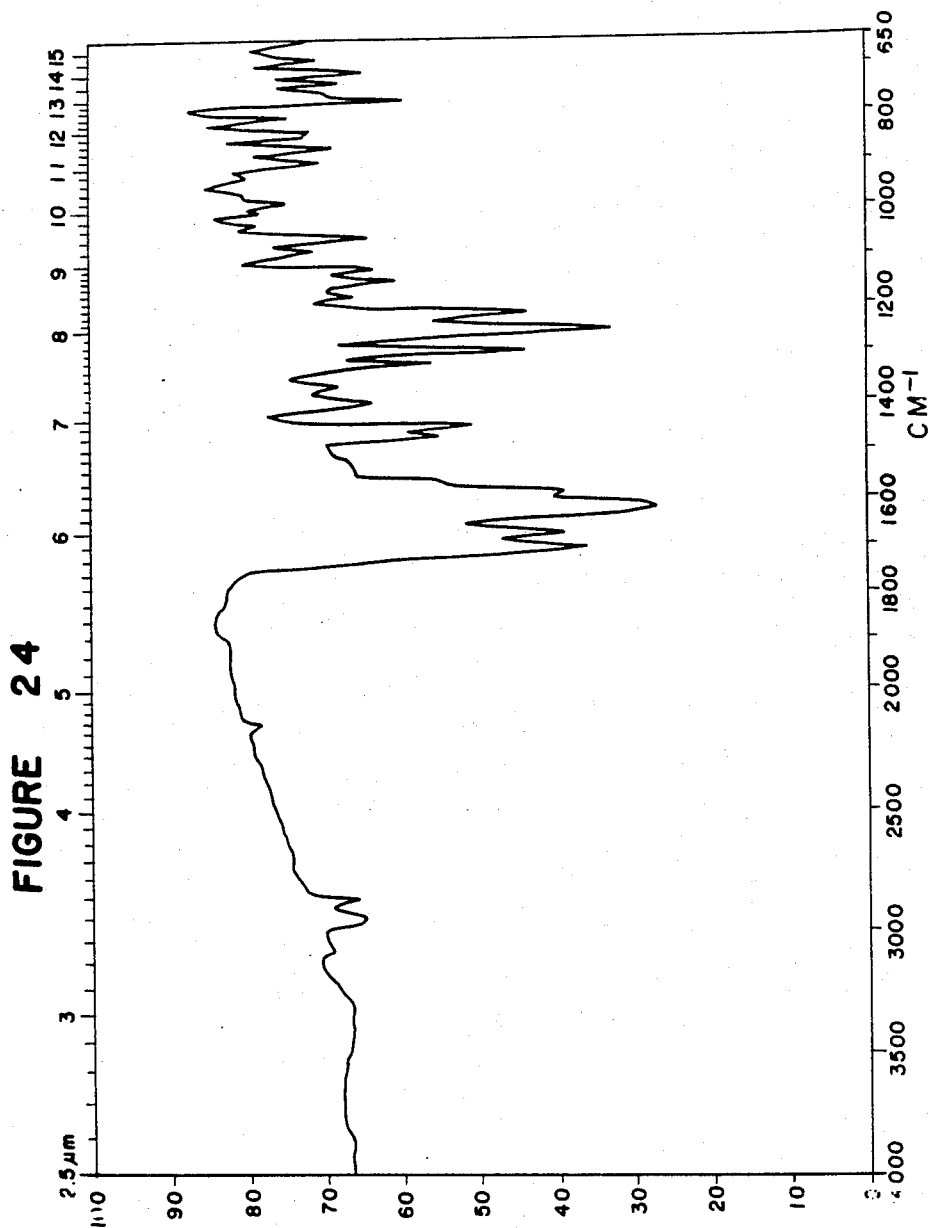
FIG. 24 is the infrared absorption spectrum of Compound No. 96.
Figure 25:
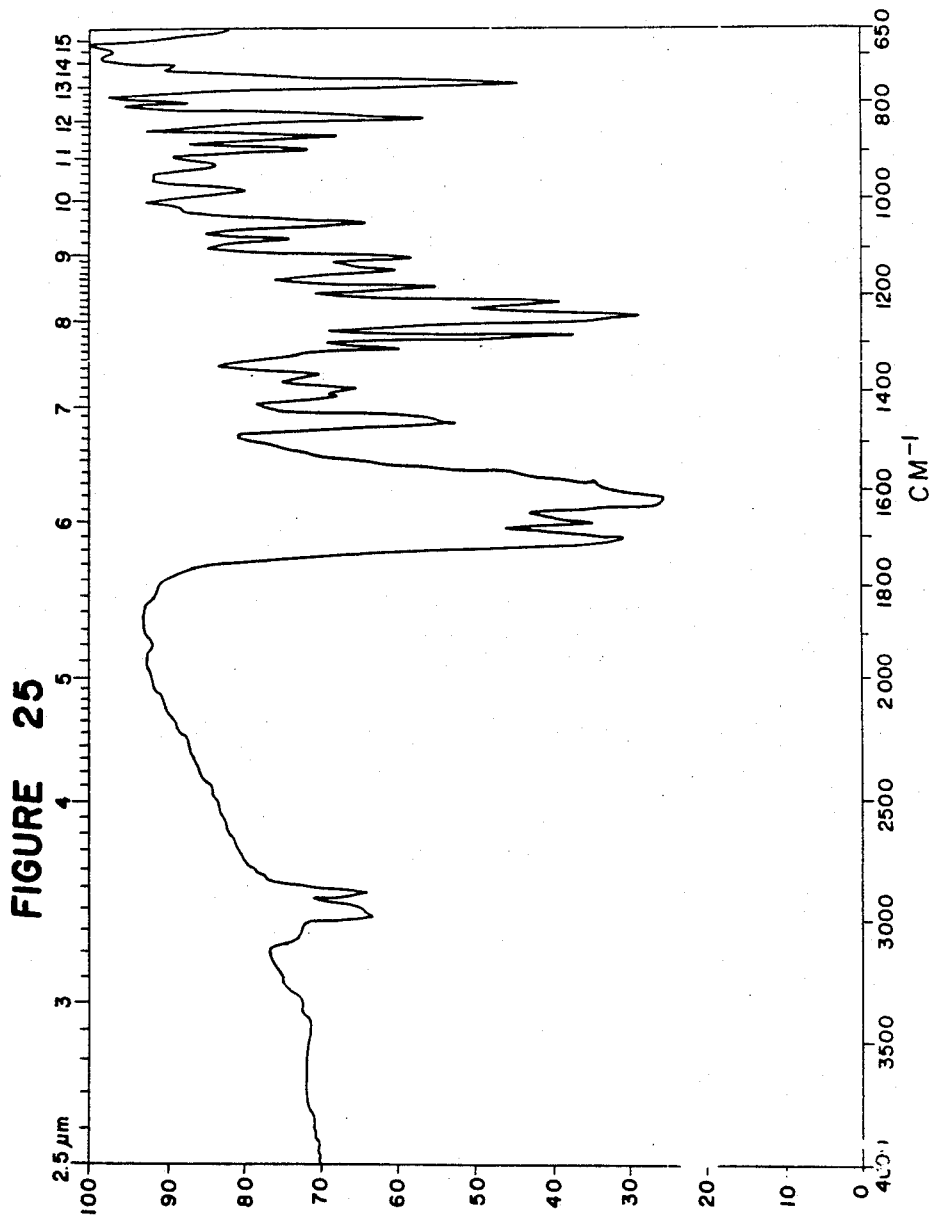
FIG. 25 is the infrared absorption spectrum of Compound No. 102.
Figure 26:
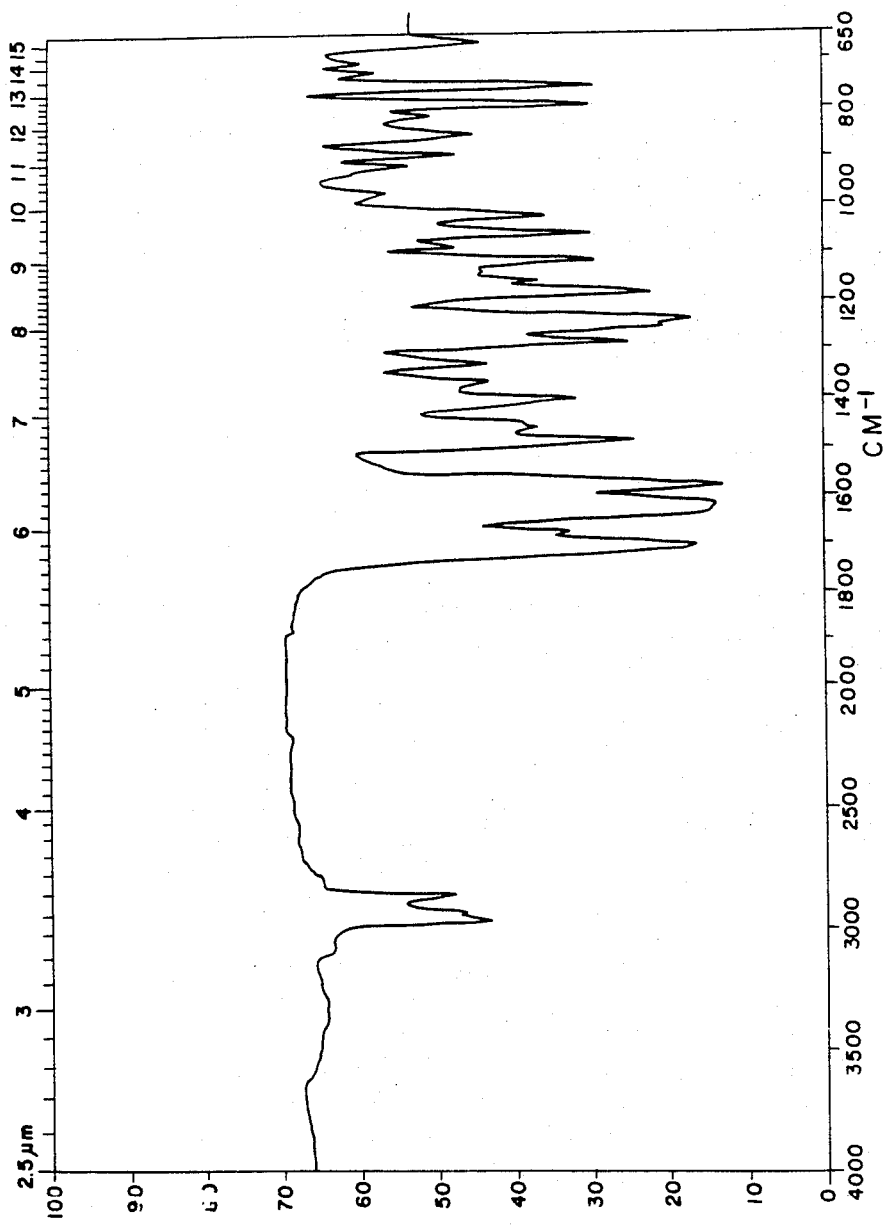
FIG. 26 is the infrared absorption spectrum of Compound No. 144.
Figure 27:
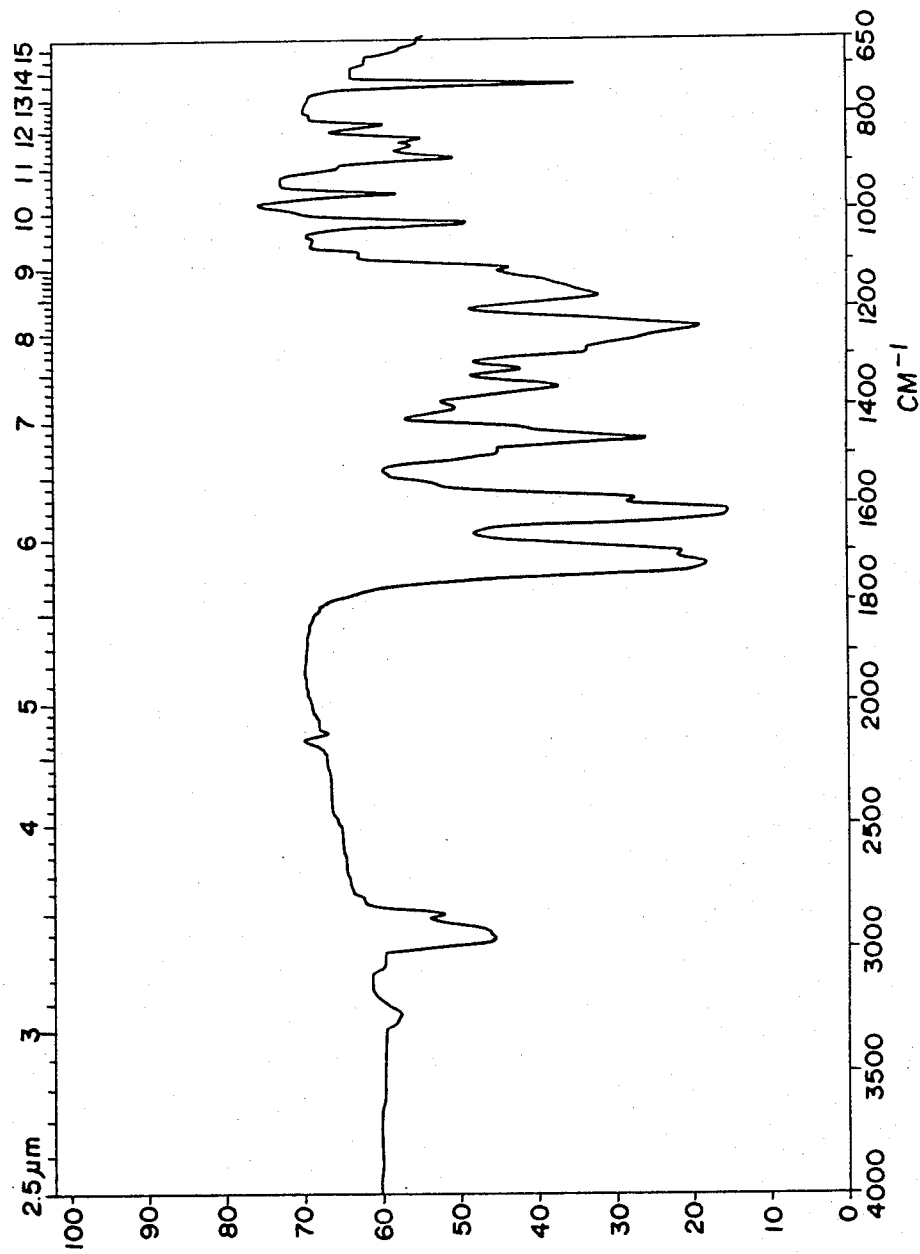
FIG. 27 is the infrared absorption spectrum of Compound No. 147.
Figure 28:
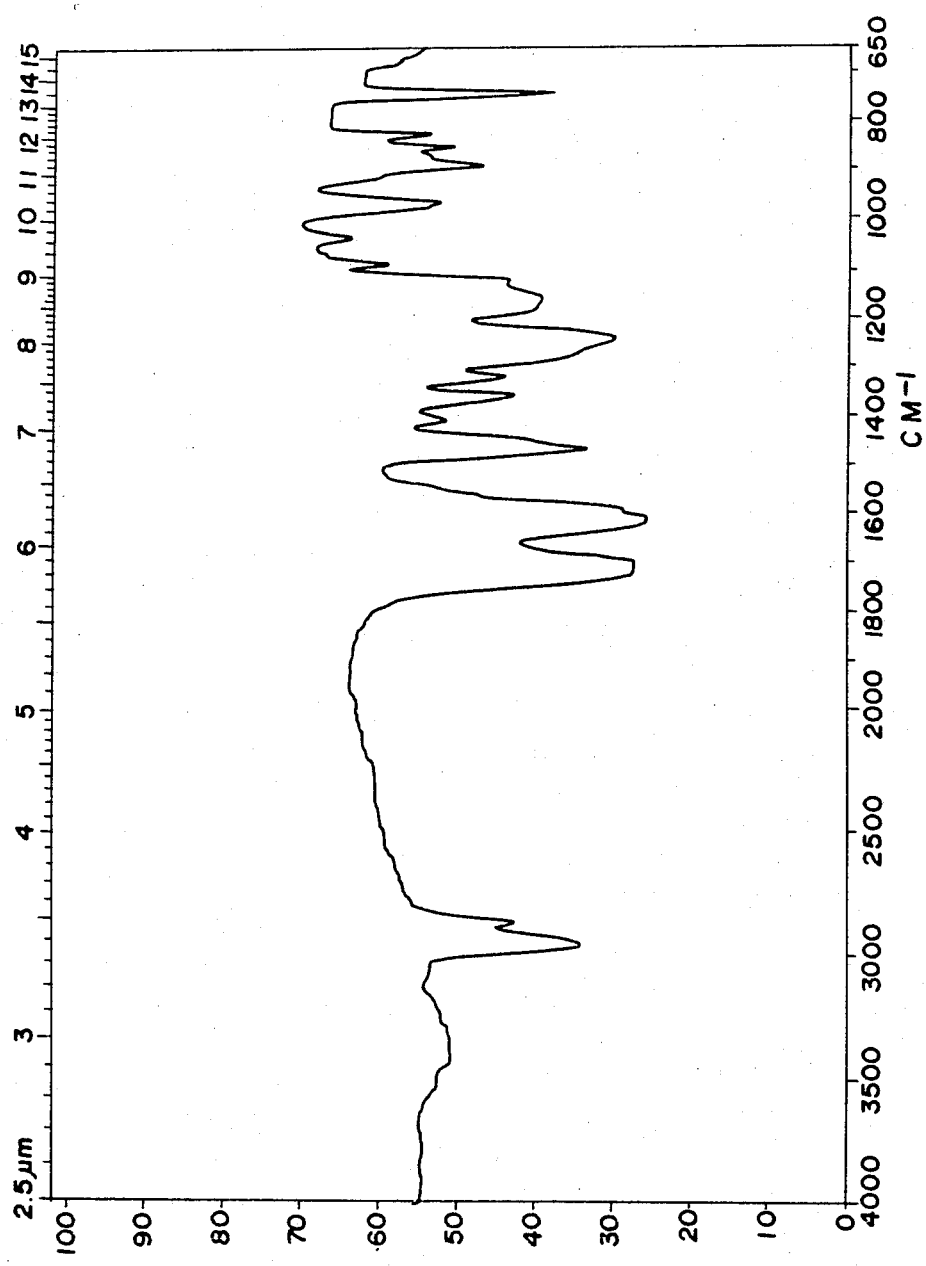
FIG. 28 is the infrared absorption spectrum of Compound No. 148.
Figure 29:
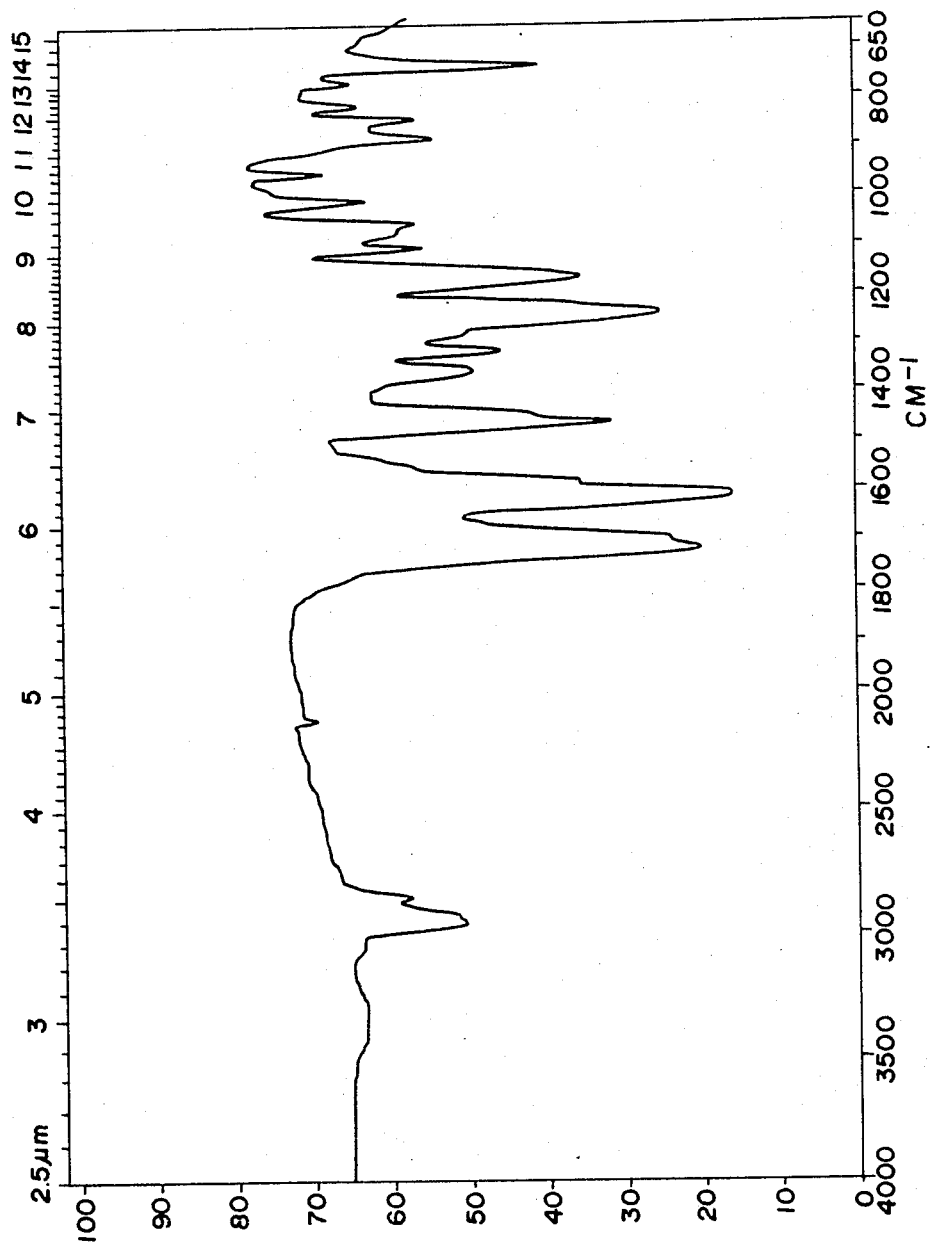
FIG. 29 is the infrared absorption spectrum of Compound No. 149.
Figure 30:
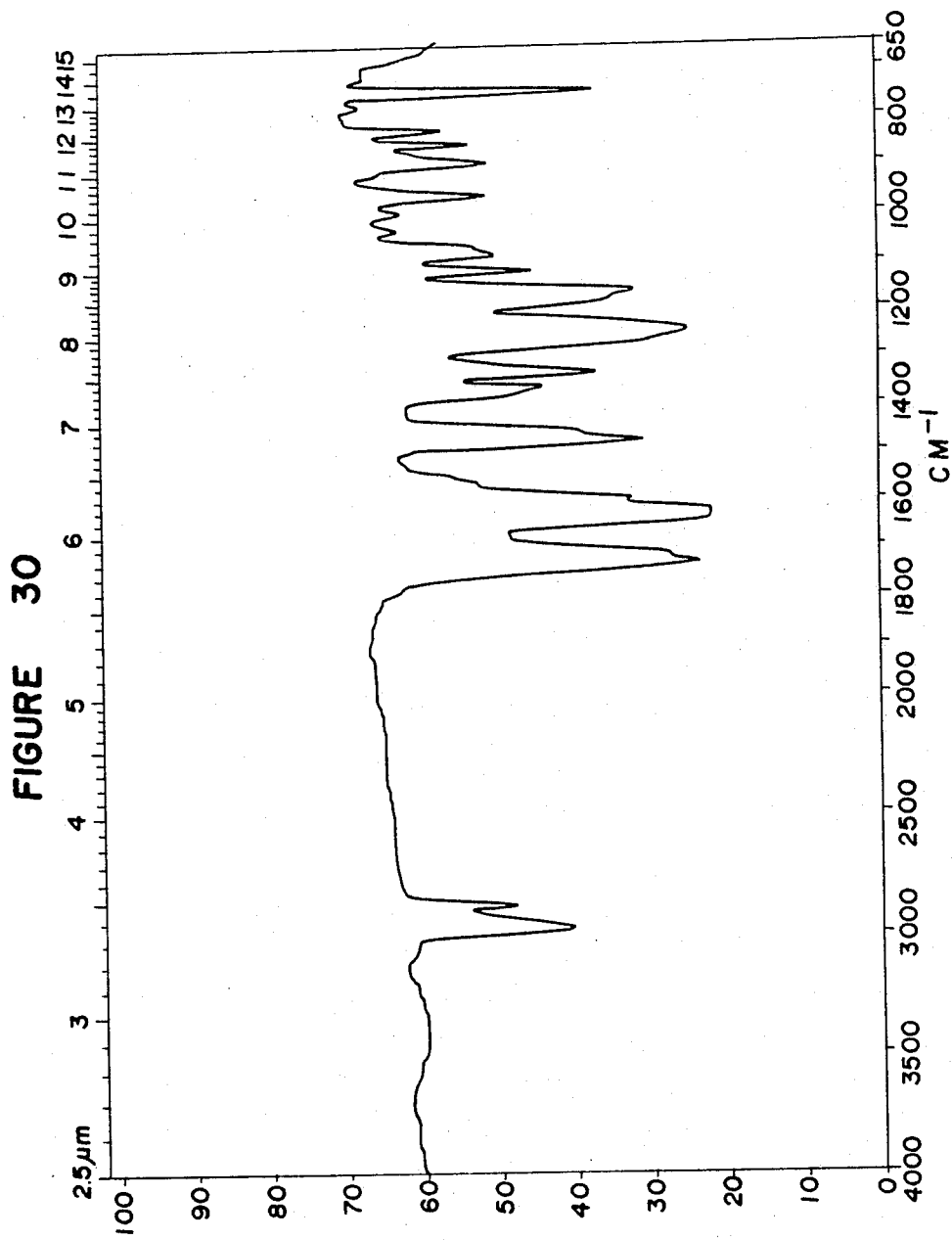
FIG. 30 is the inrared absorption spectrum of Compound No. 150.
Figure 31:
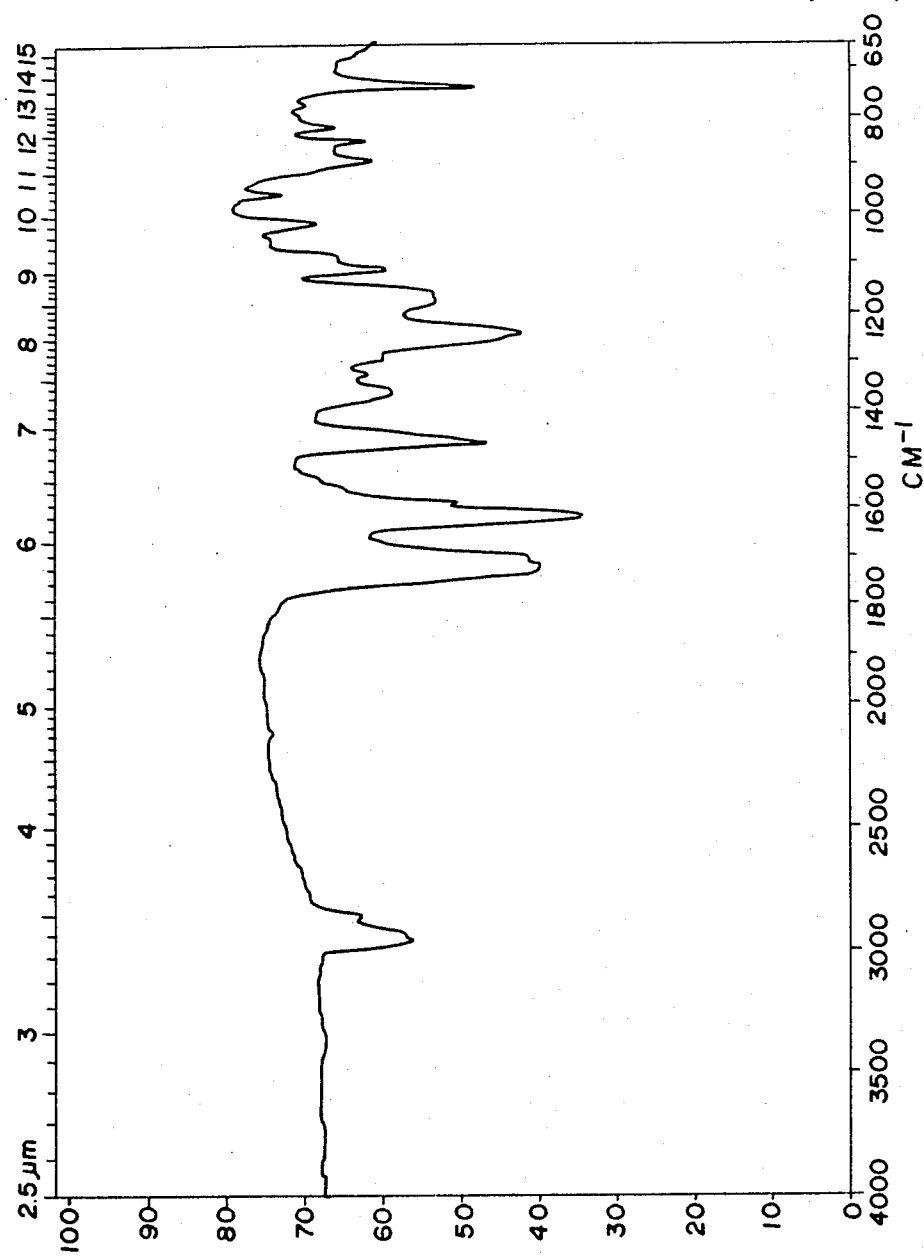
FIG. 31 is the infrared absorption spectrum of Compound No. 151.
Figure 32:
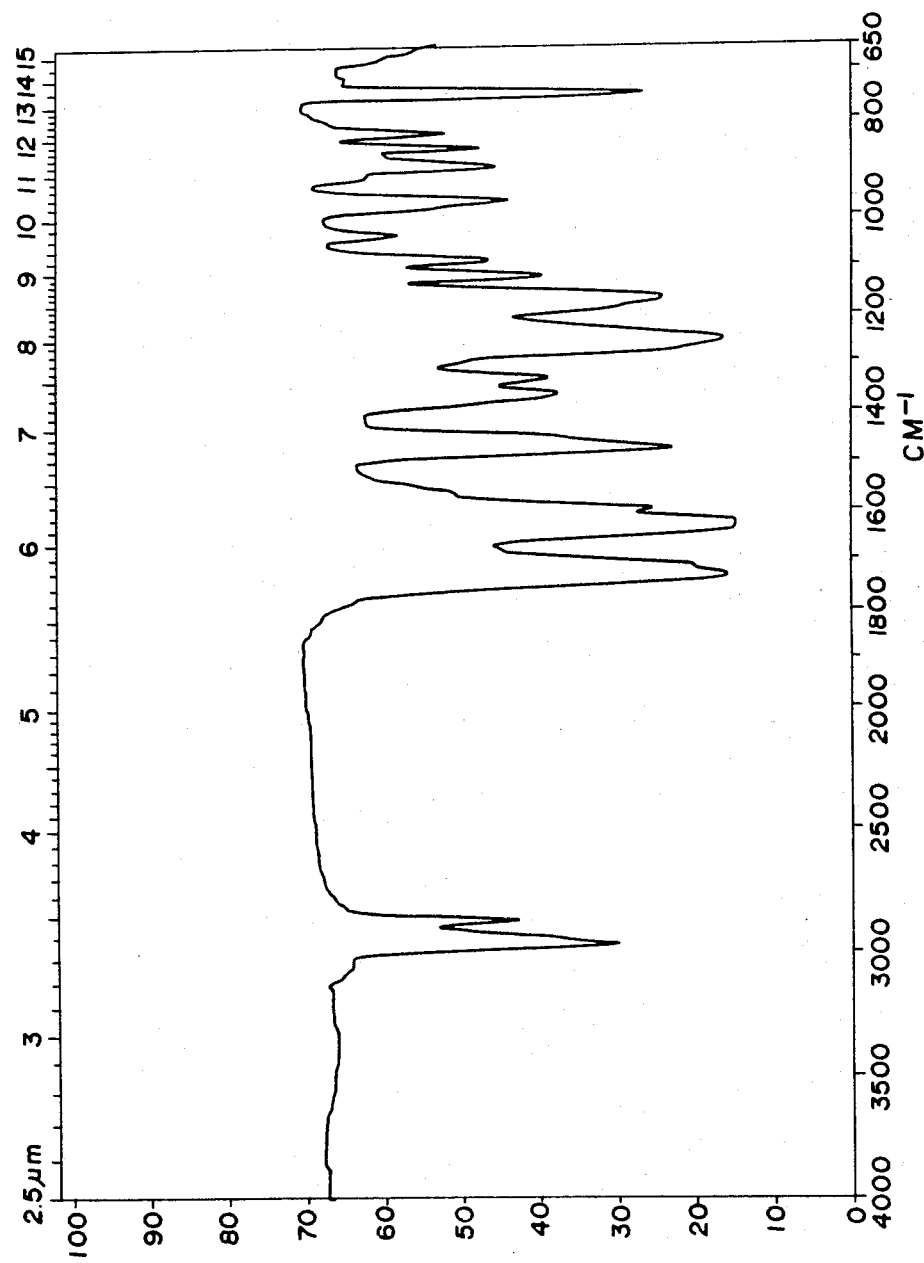
FIG. 32 is the infrared absorption spectrum of Compound No. 152.
Figure 33:
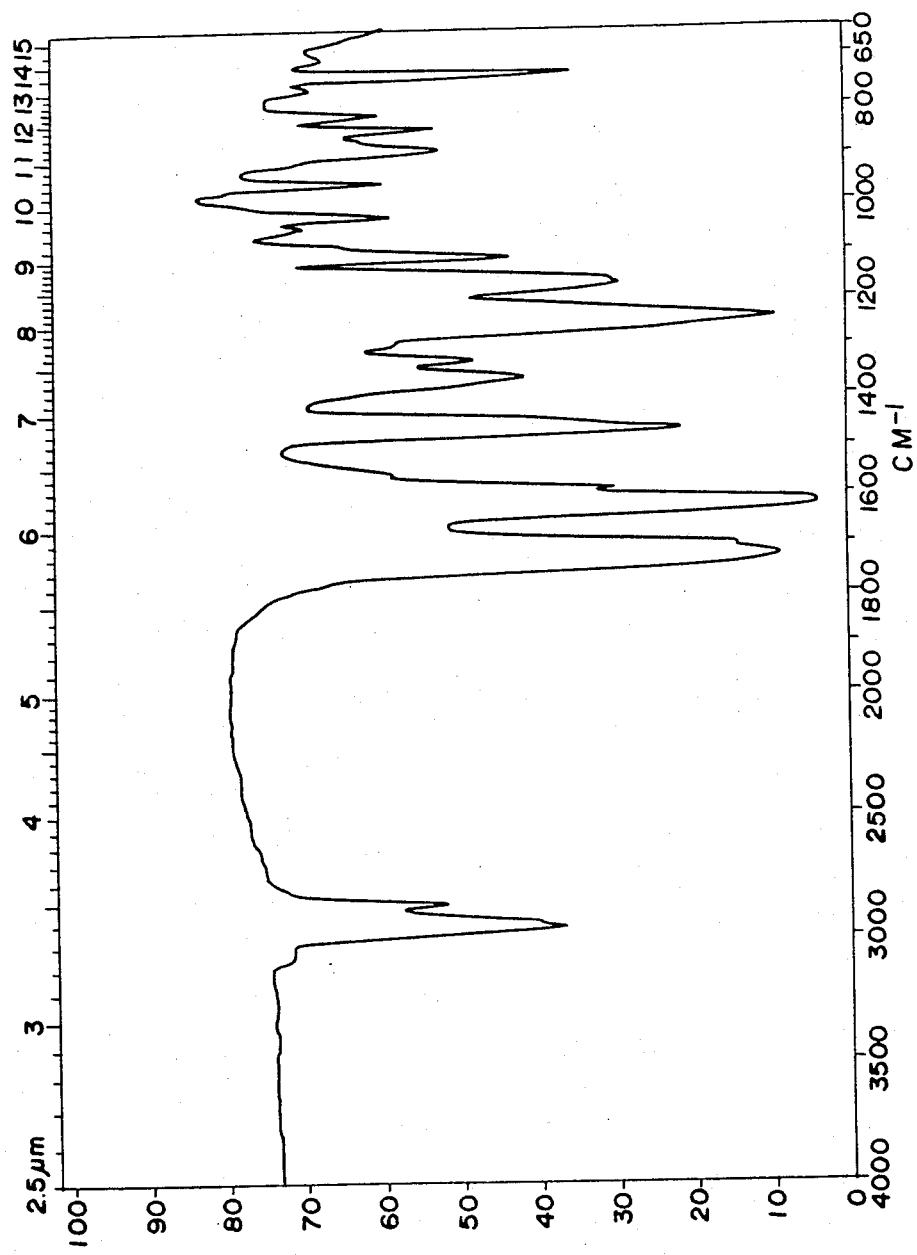
FIG. 33 is the infrared absorption spectrum of Compound No. 153.
Figure 34:
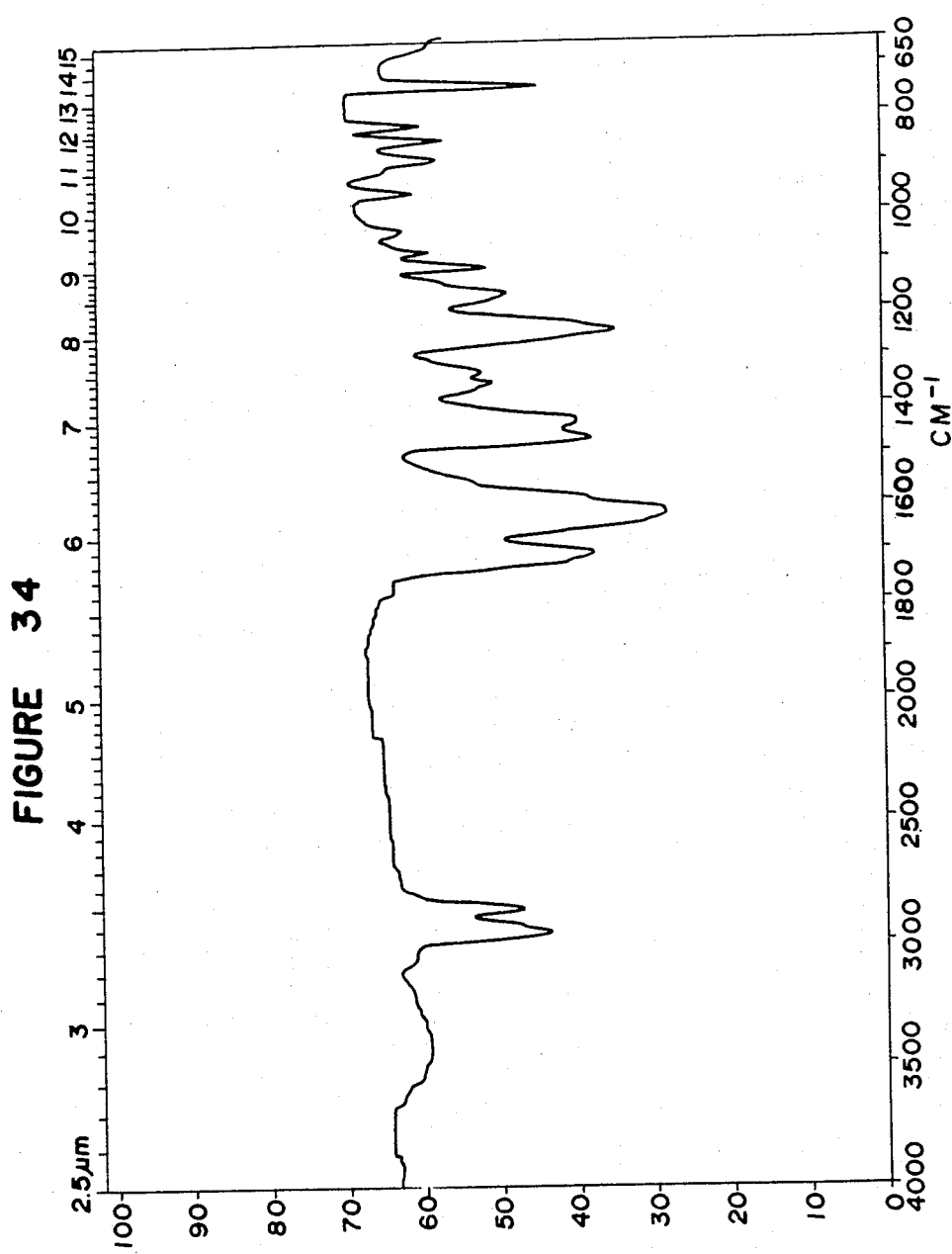
FIG. 34 is the infrared absorption spectrum of Compound No. 155.
Figure 35:
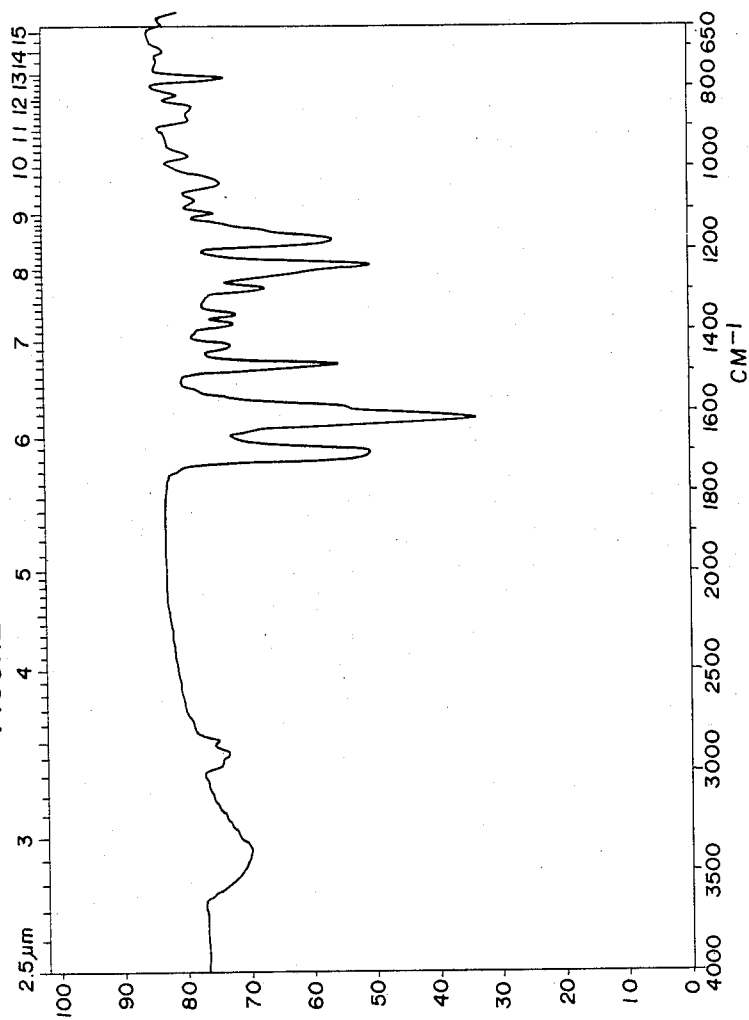
FIG. 35 is the infrared absorption spectrum of Compound No. 157.

In the formula I, Y is preferably halogen, alkoxy which may be substituted by halogen, alkenyloxy which may be substituted by halogen, alkynyloxy, phenoxy, benzyloxy which may be substituted by chlorine or alkyl,

[wherein $R_1$ is hydrogen, alkyl, phenyl, cycloalkyl, alkoxyalkyl, alkoxycarbonylalkyl or

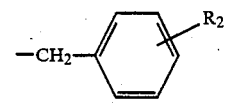

(wherein $R_2$ is hydrogen or alkoxy), X is oxygen or sulfur],

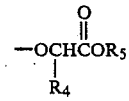

[wherein $R_4$ is hydrogen or alkyl, and $R_5$ is hydrogen, alkyl, alkynyl, benzyl, alkoxyalkyl, tetrahydrofurfuryl, alkoxyalkyloxyalkyl, alkoxycarbonylalkyl, cycloalkyl or —N=C(CH$_3$)R$_6$ (wherein R$_6$ is alkyl or phenyl)].

A compound having the formula:

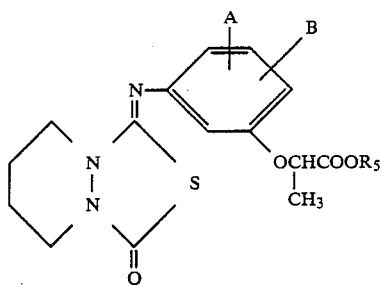

wherein A is hydrogen or halogen, B is halogen, and $R_5$ is hydrogen, alkyl, alkynyl, benzyl, alkoxyalkyl, tetrahydrofurfuryl, alkoxyalkyloxyalkyl, alkoxycarbonylalkyl, cycloalkyl, or $-N=C(CH_3)R_6$ (wherein $R_6$ is alkyl or phenyl), is effective particularly as a herbicide for a soybean field. Particularly preferred in this respect is a compound of the formula:

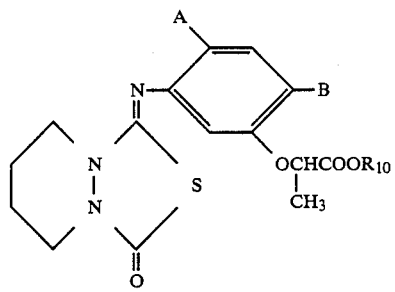

wherein A is hydrogen or halogen, B is halogen, and $R_{10}$ is hydrogen, alkyl, alkynyl, alkoxyalkyl, alkoxyalkyloxyalkyl, or tetrahydrofurfuryl.

As a herbicide for a non-agricultural field, a compound of the formula:

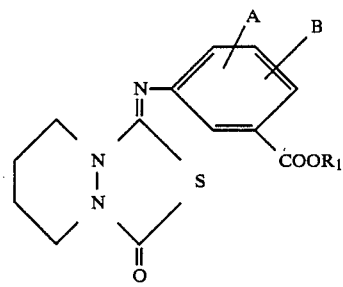

wherein A is hydrogen or halogen, B is halogen, and $R_1$ is hydrogen, alkyl, phenyl, cycloalkyl, alkoxyalkyl, alkoxycarbonylalkyl or

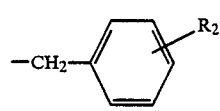

(wherein $R_2$ is hydrogen or alkoxy), is particularly useful. Particularly preferred in this respect is a compound having the formula:

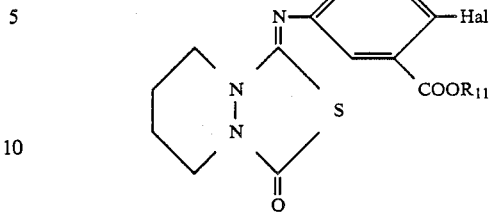

wherein Hal is halogen, and $R_{11}$ is hydrogen or alkyl.

Typical examples of the compound of the formula I are presented in Table 1.

TABLE 1

| Compound No. | X | $Y_n$ |
|---|---|---|
| 1 | O | H |
| 2 | O | 2-CH$_3$ |
| 3 | O | 2-OCH$_3$ |
| 4 | O | 2-F |
| 5 | O | 2-Cl |
| 6 | O | 3-CH$_3$ |
| 7 | O | 3-Cl |
| 8 | O | 3-CF$_3$ |
| 9 | O | 4-CH$_3$ |
| 10 | O | 4-OCH$_3$ |
| 11 | O | 4-F |
| 12 | O | 4-Cl |
| 13 | O | 4-Br |
| 14 | O | 4-I |
| 15 | O | 4-OCH$_2$—C$_6$H$_4$—Cl (para) |
| 16 | O | 2-F, 4-Cl |
| 17 | O | 2-F, 4-Br |
| 18 | O | 3-OCH$_3$, 4-Cl |
| 19 | O | 3-OC$_2$H$_5$, 4-Cl |
| 20 | O | 3-OC$_3$H$_7$—n, 4-Cl |
| 21 | O | 3-OC$_3$H$_7$—i, 4-Cl |
| 22 | O | 3-OCH$_2$CH=CH$_2$, 4-Cl |
| 23 | O | 3-OCH$_2$C≡CH, 4-Cl |
| 24 | O | 3-OC$_4$H$_9$—s, 4-Cl |
| 25 | O | 3-Cyclopentoxy, 4-Cl |
| 26 | O | 3-O—C$_6$H$_5$, 4-Cl |
| 27 | O | 3-OCH$_2$—C$_6$H$_5$, 4-Cl |
| 28 | O | 3-OCH(CH$_3$)CO$_2$—C$_2$H$_5$, 4-Cl |
| 29 | O | 3-OCH$_2$CO$_2$C$_2$H$_5$, 4-Cl |
| 30 | O | 3,4-Cl$_2$ |
| 31 | O | 3-OCH$_3$, 4-Br |
| 32 | O | 3-OCH$_2$C≡CH, 4-Br |
| 33 | O | 2-F, 4-Cl, 5-OC$_3$H$_7$—i |
| 34 | O | 2-F, 4-Cl, 5-OCH$_2$CH=CH$_2$ |
| 35 | O | 2-F, 4-Cl, 5-OCH$_2$C≡CH |
| 36 | O | 2-F, 4-Cl, 5-OCH(CH$_3$)CO$_2$—C$_2$H$_5$ |
| 37 | O | 2-F, 4-Cl, 5-OCH$_2$—C$_6$H$_5$ |
| 38 | O | 2-F, 4-Cl, 5-O—C$_6$H$_5$ |
| 39 | O | 2,4-Cl$_2$, 5-OC$_3$H$_7$—i |
| 40 | O | 2,4-Cl$_2$, 5-O—C$_6$H$_5$ |
| 41 | S | 4-Cl |
| 42 | S | 3-OC$_3$H$_7$—i, 4-Cl |
| 43 | S | 2-F, 4-Cl, 5-OC$_3$H$_7$—i |
| 44 | S | 2-F, 4-Cl, 5-O—C$_6$H$_5$ |
| 45 | S | 2,4-Cl$_2$, 5-OC$_3$H$_7$—i |
| 46 | O | 3-OH, 4-Cl |
| 47 | O | 2-F, 4-Cl, 5-OCH$_2$CO$_2$C$_2$H$_5$ |
| 48 | O | 3-OC$_4$H$_9$—n, 4-Cl |
| 49 | O | 2-F, 4-Cl, 5-OC$_4$H$_9$—s |
| 50 | O | 3-OCH(CH$_3$)CO$_2$—CH$_2$C≡CH, 4-Cl |
| 51 | O | 3-OC$_5$H$_{11}$—n, 4-Cl |
| 52 | O | 3-OC$_5$H$_{11}$—s, 4-Cl |
| 53 | O | 3-OC$_4$H$_9$—i, 4-Cl |
| 54 | O | 4-CF$_3$ |
| 55 | O | 3-OC$_8$H$_{17}$—n, 4-Cl |
| 56 | O | 3-OCH(CH$_3$)CO$_2$—CH$_2$—C$_6$H$_5$, 4-Cl |
| 57 | O | 3-OCH$_2$CH=CH—CH$_3$, 4-Cl |
| 58 | O | 3-OC$_3$H$_7$—i, 4-Br |
| 59 | O | 3-OCH(CH$_3$)CO$_2$—C$_4$H$_9$—n, 4-Cl |

TABLE 1-continued

| Compound No. | X | $Y_n$ |
|---|---|---|
| 60 | O | 3-OC$_2$H$_4$CH=CH$_2$, 4-Cl |
| 61 | O | 3-OCH$_2$C(CH$_3$)=CH$_2$, 4-Cl |
| 62 | O | 3-OCH$_2$—C$_6$H$_4$—Cl (para), 4-Cl |
| 63 | O | 3-OC$_4$H$_9$—i, 4-Br |
| 64 | O | 3-OCH$_2$CH=CH$_2$, 4-Br |
| 65 | O | 3-OCH$_2$—C$_6$H$_4$—Cl (ortho), 4-Cl |
| 66 | O | 3-OCH$_2$—C$_6$H$_4$—CH$_3$ (para), 4-Cl |
| 67 | O | 2-F, 4-Cl, 5-CH$_2$OCH$_3$ |
| 68 | O | 3-OCH$_2$CH=C(CH$_3$)$_2$, 4-Cl |
| 69 | O | 3-OCH(CH$_3$)COS—C$_2$H$_5$, 4-Cl |
| 70 | O | 3-OCH(CH$_3$)CO$_2$—C$_4$H$_9$—i, 4-Cl |
| 71 | O | 3-OCH(CH$_3$)CO$_2$C$_2$H$_4$OCH$_3$, 4-Cl |
| 72 | O | 3-NHCH(CH$_3$)CO$_2$C$_2$H$_5$, 4-Cl |
| 73 | O | 3-OC$_2$H$_4$Cl, 4-Cl |
| 74 | O | 3-OCH$_2$—C$_6$H$_4$—Cl (metha), 4-Cl |
| 75 | O | 3-OCH(CH$_3$)—C$_6$H$_5$, 4-Cl |
| 76 | O | 3-CH$_2$OC$_2$H$_5$, 4-Cl |
| 77 | O | 3-Cyclohexyloxy, 4-Cl |
| 78 | O | 3-Cyclohexylmethyloxy, 4-Cl |
| 79 | O | 3-OC$_2$H$_4$C≡CH, 4-Cl |
| 80 | O | 3-(1-Cyclohexyloxycarbonylethoxy), 4-Cl |
| 81 | O | 3-OCH(CH$_3$)CH=CH$_2$, 4-Cl |
| 82 | O | 2-F, 4-Cl, 5-OCH$_2$—C$_6$H$_4$—Cl (para) |
| 83 | O | 2-Br, 4-Cl, 5-OCH$_2$CO$_2$C$_2$H$_5$ |
| 84 | O | 3-OCH(CH$_3$)CO$_2$N=C(CH$_3$)$_2$, 4-Cl |
| 85 | O | 3-OPO(OC$_2$H$_5$)$_2$, 4-Cl |
| 86 | O | 2,4-Cl$_2$, 5-OCH(CH$_3$)CO$_2$C$_2$H$_5$ |
| 87 | O | 3-CH$_2$OCH$_2$C≡CH, 4-Cl |
| 88 | O | 3-OCONHC$_2$H$_5$, 4-Cl |
| 89 | O | 3-NHCOC$_2$H$_5$, 4-Cl |
| 90 | O | 3-OCONHCH$_3$, 4-Cl |
| 91 | O | 3,5-Cl$_2$ |
| 92 | O | 3-OCH(CH$_3$)CO$_2$—N=C(CH$_3$)C$_6$H$_5$, 4-Cl |
| 93 | O | 3-CH$_2$—C$_6$H$_5$, 4-Cl |
| 94 | O | 3-OCH$_2$CH=CHCl, 4-Cl |
| 95 | O | 3-CO$_2$C$_2$H$_5$, 4-Cl |
| 96 | O | 3-COC$_6$H$_5$, 4-Cl |
| 97 | O | 3-CO$_2$—C$_3$H$_7$—i, 4-Cl |
| 98 | O | 3-CO$_2$—C$_4$H$_9$—n, 4-Cl |
| 99 | O | 3-C$_3$H$_7$—n, 4-Cl |
| 100 | O | 3-CH$_2$—C$_6$H$_4$—CH$_3$ (para), 4-Cl |
| 101 | O | 3-CH$_2$—C$_6$H$_3$—(CH$_3$)$_2$(2,5), 4-Cl |
| 102 | O | 3-CO—C$_6$H$_4$—CH$_3$ (para), 4-Cl |
| 103 | O | 3-CH=CHCH$_3$, 4-Cl |
| 104 | O | 3-SC$_2$H$_5$, 4-Cl |
| 105 | O | 3-SO$_2$C$_2$H$_5$, 4-Cl |
| 106 | O | 3-Pyrrolidinocarbonyl, 4-Cl |
| 107 | O | 3-CO$_2$—CH(CH$_3$)CO$_2$C$_2$H$_5$, 4-Cl |
| 108 | O | 3-CO$_2$—C$_2$H$_4$OCH$_3$, 4-Cl |
| 109 | O | 3-SCH$_2$=CH$_2$, 4-Cl |
| 110 | O | 3-SCH$_2$C≡CH, 4-Cl |
| 111 | O | 3-SO$_2$CH$_2$CH=CH$_2$, 4-Cl |
| 112 | O | 2-F, 4-Cl, 5-CO$_2$C$_2$H$_5$ |
| 113 | O | 3-Cyclopentoxycarbonyl, 4-Cl |
| 114 | O | 3-COSC$_2$H$_5$, 4-Cl |
| 115 | O | 3-CH$_2$CN, 4-Cl |
| 116 | O | 3-CO$_2$—C$_6$H$_5$, 4-Cl |
| 117 | O | 3-CO$_2$—CH$_2$—C$_6$H$_5$, 4-Cl |
| 118 | O | 3-OCH$_2$CH=CCl$_2$, 4-Cl |
| 119 | O | 2-F, 4-Cl, 5-CO$_2$—CH$_2$C$_6$H$_4$—OCH$_3$ (para) |
| 120 | O | 2-F, 4-Cl, 5-CO$_2$H |
| 121 | O | 2-F, 4-Cl, 5-CO$_2$—C$_3$H$_7$—i |
| 122 | O | 2-F, 4-Cl, 5-OCH(CH$_3$)CO$_2$CH$_3$ |
| 123 | O | 2-F, 4-Cl, 5-OCH(CH$_3$)CO$_2$—C$_3$H$_7$—i |
| 124 | O | 2-F, 4-Cl, 5-OCH(CH$_3$)CO$_2$—C$_4$H$_9$—i |
| 125 | O | 2-F, 4-Cl, 5-OCH(CH$_3$)CO$_2$—CH$_2$C≡CH |
| 126 | O | 2-F, 4-Cl, 5-OCH(CH$_3$)CO$_2$—N=C=(CH$_3$)$_2$ |
| 127 | O | 2-F, 4-Cl, 5-OCH(CH$_3$)CO$_2$—N=C.(CH$_3$)—C$_6$H$_5$ |
| 128 | O | 2-F, 4-Cl, 5-OCH(CH$_3$)CO$_2$—C$_2$H$_4$OCH$_3$ |
| 129 | O | 2-F, 4-Cl, 5-OCH(CH$_3$)CO$_2$—C$_2$H$_4$—OC$_2$H$_5$ |
| 130 | O | 2-F, 4-Cl, 5-OCH(CH$_3$)CO$_2$—C$_2$H$_4$—OC$_3$H$_7$—i |
| 131 | O | 2-F, 4-Cl, 5-OCH(CH$_3$)CO$_2$—C$_2$H$_4$—OC$_4$H$_9$—n |
| 132 | O | 2-F, 4-Cl, 5-OCH(CH$_3$)CO$_2$—C$_2$H$_4$—OC$_2$H$_4$OCH$_3$ |
| 133 | O | 2-F, 4-Cl, 5-OCH(CH$_3$)CO$_2$—CH.(CH$_3$)CH$_2$OCH$_3$ |
| 134 | O | 2-F, 4-Cl, 5-OCH(CH$_3$)CO$_2$—C$_3$H$_6$—OC$_2$H$_5$ |
| 135 | O | 2-F, 4-Cl, 5-(1-Tetrahydrofuryloxy-carbonylethoxy) |
| 136 | O | 2-F, 4-Cl, 5-OCH(CH$_3$)CO$_2$—CH$_2$—CO$_2$C$_2$H$_5$ |
| 137 | O | 2-F, 4-Cl, 5-OCH(CH$_3$)CO$_2$—CH.(CH$_3$)CO$_2$CH$_3$ |
| 138 | O | 2-F, 4-Cl, 5-OCH(CH$_3$)CO$_2$—CH.(CH$_3$)CO$_2$C$_2$H$_5$ |
| 139 | O | 3-OPS(OC$_2$H$_5$)$_2$, 4-Cl |
| 140 | O | 3-OC$_2$H$_4$C$_6$H$_5$, 4-Cl |
| 141 | O | 3-OC$_2$H$_4$OCH$_3$, 4-Cl |
| 142 | O | 3-CH$_3$, 4-Cl |
| 143 | O | 3-OCH$_2$CCl=CH$_2$, 4-Cl |
| 144 | O | 3-(2,2-Dichlorocyclopropylmethoxy), 4-Cl |
| 145 | O | 3-SCHCO$_2$C$_2$H$_5$, 4-Cl<br>    \|<br>   CH$_3$ |
| 146 | O | 3-SCHCO$_2$—⟨C$_6$H$_{11}$⟩, 4-Cl<br>    \|<br>   CH$_3$ |
| 147 | O | 2-F, 4-Cl, 5-SCH(CH$_3$)CO$_2$C$_2$H$_5$ |
| 148 | O | 2-F, 4-Cl, 5-SCH$_2$CO$_2$—⟨C$_6$H$_{11}$⟩ |
| 149 | O | 2-F, 4-Cl, 5-SCH(CH$_3$)CO$_2$C$_2$H$_5$ |
| 150 | O | 2-F, 4-Cl, 5-SCH(CH$_3$)CO$_2$—⟨C$_5$H$_9$⟩ |
| 151 | O | 2-F, 4-Cl, 5-SCH(C$_2$H$_5$)CO$_2$C$_2$H$_5$ |
| 152 | O | 2-F, 4-Cl, 5-SCH(C$_2$H$_5$)CO$_2$—⟨C$_5$H$_9$⟩ |
| 153 | O | 2-F, 4-Cl, 5-SCH(C$_3$H$_7$)CO$_2$C$_2$H$_5$ |
| 154 | O | 2-F, 4-Cl, 5-SCH(CH$_3$)CON⟨ ⟩ |
| 155 | | 2-F, 4-Cl, 5-SCH(C$_2$H$_5$)CON⟨ ⟩ |
| 156 | O | 2-F, 4-Cl, 5-OCH(CH$_3$)CO$_2$H |
| 157 | O | 2-F, 4-Cl, 5-OCH(CH$_3$)CH=CHCO$_2$C$_2$H$_5$ |
| 158 | O | 2-F, 4-Cl, 5-CO$_2$CH$_3$ |
| 159 | O | 2-F, 4-Cl, 5-CO$_2$C$_3$H$_7$—n |
| 160 | O | 2-F, 4-Cl, 5-CO$_2$C$_4$H$_9$—n |

The melting points and refractive indexes of the Compound Nos. 1 to 157 are shown in Table 2.

TABLE 2

| Compound No. | Melting point (°C.) | Refractive index $n_D^{20}$ |
|---|---|---|
| 1 | 78–82 | |
| 2 | 74–78 | |
| 3 | | 1.6124 |
| 4 | 83–85 | |
| 5 | 73–75 | |
| 6 | | 1.6208 |
| 7 | | 1.6368 |
| 8 | | 1.5641 |
| 9 | | 1.6256 |

TABLE 2-continued

| Compound No. | Melting point (°C.) | Refractive index $n_D^{20}$ |
|---|---|---|
| 10 | 116–119 | |
| 11 | 69–72 | |
| 12 | 82–85 | |
| 13 | 69–70 | |
| 14 | 80–82 | |
| 15 | 150–154 | |
| 16 | | 1.6121 |
| 17 | 98–100 | |
| 18 | 125–128 | |
| 19 | 143–145 | |
| 20 | 102–105 | |
| 21 | 66–69 | |
| 22 | 119–122 | |
| 23 | 130–132 | |
| 24 | | 1.5794 |
| 25 | | 1.6145 |
| 26 | 83–85 | |
| 27 | 114–116 | |
| 28 | | 1.5840 |
| 29 | 94–96 | |
| 30 | 116–118 | |
| 31 | 118–121 | |
| 32 | 132–135 | |
| 33 | | Not measurable |
| 34 | 106–109 | |
| 35 | 132–134 | |
| 36 | | 1.5666 |
| 37 | 99–101 | |
| 38 | 116–119 | |
| 39 | | 1.6050 |
| 40 | 111–114 | |
| 41 | 96–97 | |
| 42 | 98–101 | |
| 43 | 77–80 | |
| 44 | 138–141 | |
| 45 | 71–73 | |
| 46 | 130–132 | |
| 47 | 93–96 | |
| 48 | | 1.6050 |
| 49 | | Not measurable |
| 50 | | 1.5915 |
| 51 | | 1.5951 |
| 52 | | 1.5878 |
| 53 | 72–75 | |
| 54 | 103–107 | |
| 55 | | 1.5673 |
| 56 | | 1.5961 |
| 57 | 83–86 | |
| 58 | 84–88 | |
| 59 | | 1.5732 |
| 60 | 77–78 | |
| 61 | 89–95 | |
| 62 | 94–96 | |
| 63 | 92–95 | |
| 64 | 116–119 | |
| 65 | 100–103 | |
| 66 | 162–164 | |
| 67 | 84–87 | |
| 68 | 78–81 | |
| 69 | | 1.5962 |
| 70 | | 1.5661 |
| 71 | | 1.5710 |
| 72 | | 1.5755 |
| 73 | 110–114 | |
| 74 | 120–122 | |
| 75 | | Not measurable |
| 76 | 73–76 | |
| 77 | | 1.6043 |
| 78 | 97–103 | |
| 79 | 85–88 | |
| 80 | | 1.5771 |
| 81 | | 1.5970 |
| 82 | 129–132 | |
| 83 | 116–118 | |
| 84 | | Not measurable |
| 85 | | 1.5759 |
| 86 | | Not measurable |
| 87 | | 1.6046 |
| 88 | 143–146 | |
| 89 | 117–120 | |
| 90 | 167–170 | |
| 91 | 111–114 | |
| 92 | 44–46 | |
| 93 | 154–156 | |
| 94 | 87–90 | |
| 95 | | 1.6043 |
| 96 | | Not measurable |
| 97 | | 1.5843 |
| 98 | | 1.5775 |
| 99 | | 1.5678 |
| 100 | | 1.6255 |
| 101 | 127–129 | |
| 102 | | Not measurable |
| 103 | | 1.6320 |
| 104 | 120–122 | |
| 105 | | 1.6213 |
| 106 | 119–121 | |
| 107 | | 1.5881 |
| 108 | | 1.5936 |
| 109 | 66–68 | |
| 110 | | 1.6641 |
| 111 | | 1.6225 |
| 112 | | 1.6002 |
| 113 | | 1.5979 |
| 114 | | 1.6321 |
| 115 | 120–122 | |
| 116 | | 1.6297 |
| 117 | | 1.6024 |
| 118 | | 1.6058 |
| 119 | | 1.6052 |
| 120 | 223–226 | |
| 121 | | 1.5734 |
| 122 | 106–109 | |
| 123 | | 1.5549 |
| 124 | 69–72 | |
| 125 | | 1.5735 |
| 126 | 116–119 | |
| 127 | 52–55 | |
| 128 | | 1.5749 |
| 129 | | 1.5678 |
| 130 | | 1.5590 |
| 131 | | 1.5575 |
| 132 | | 1.5672 |
| 133 | | 1.5580 |
| 134 | | 1.5691 |
| 135 | | 1.5751 |
| 136 | | 1.5690 |
| 137 | | 1.5647 |
| 138 | | 1.5538 |
| 139 | | 1.5995 |
| 140 | 115–118 | |
| 141 | 68–71 | |
| 142 | 82–84 | |
| 143 | 77–79 | |
| 144 | | Not measurable |
| 145 | | 1.5969 |
| 146 | | 1.5972 |
| 147 | | 1.5990 |
| 148 | | Not measurable |
| 149 | | 1.5925 |
| 150 | | 1.602 |
| 151 | | 1.5738 |
| 152 | | 1.5963 |
| 153 | | 1.5761 |
| 154 | 136–138 | |
| 155 | | Not measurable |
| 156 | 120–122 | |
| 157 | | Not measurable |
| 158 | 79–81 | |
| 159 | 57–59 | |
| 160 | | 1.5791 |

The compound of the formula I may be prepared by the following processes.

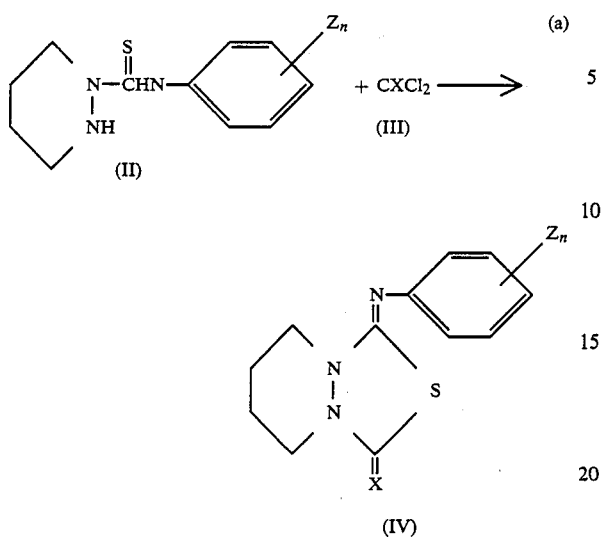

(a)

(II) + (III) →

(IV)

wherein X, Z and n are as defined above. This process can be conducted by reacting the compound of the formula II with the compound of the formula III in the presence of a base.

As the base, there may be mentioned an aliphatic tertiary amine such as triethylamine or trimethylamine; an aromatic tertiary amine such as pyridine, picoline or quinoline; or an inorganic base such as sodium hydroxide, potassium hydroxide, potassium carbonate or sodium carbonate.

The above reaction is preferably conducted in a solvent. As such a solvent, there may be mentioned a chlorine-containing hydrocarbon such as dichloromethane, chloroform or carbon tetrachloride; an ether such as diethyl ether, tetrahydrofuran or dioxane; a hydrocarbon such as n-hexane, benzene or toluene; an aliphatic ketone such as acetone or methyl ethyl ketone; dimethylsulfoxide; or N,N-dimethylformamide.

The above-mentioned condensation reaction can be completed in from 1 to 7 hours at a temperature within a range of from −20° C. to the boiling point of the solvent. (b)

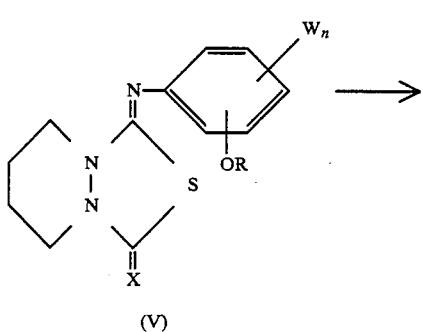

(V)

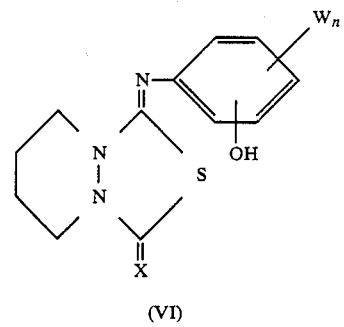

(VI)

wherein X, W, R and n are as defined above.

This process can be conducted by reacting the compound of the formula V with an acid such as hydrobromic acid or aluminum chloride in the presence of a solvent, for instance, a fluorine-containing hydrocarbon such as chloroform or carbon tetrachloride, or a hydrocarbon such as benzene or toluene. This reaction can be completed in from 1 to 7 hours at a temperature within a range of from 0° C. to the boiling point of the solvent.

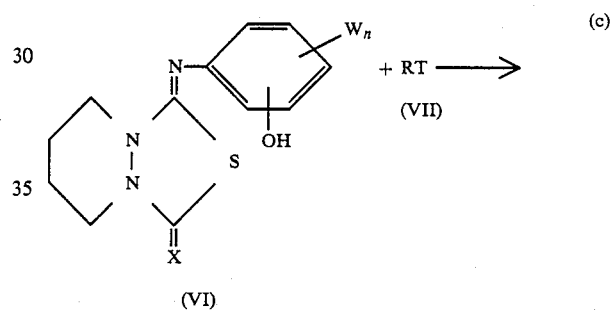

(VI) + RT → (VII)

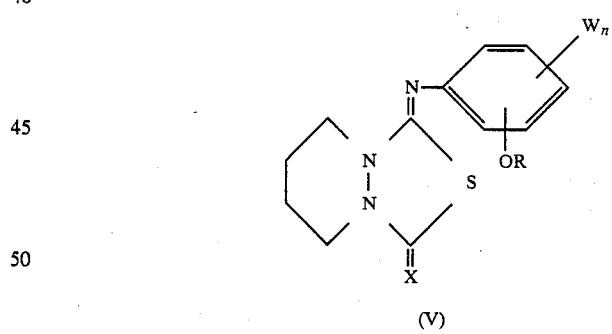

(V)

wherein W, X, R, T and n are as defined above.

This process can be conducted by reacting the compound of the formula VI with the compound of the formula VII in the presence of the same base and solvent as used in process (a) at a temperature within a range of from −20° C. to the boiling point of the solvent for from 1 to 7 hours.

Now, the present invention will be described in further detail with reference to Examples. However, it should be understood that the present invention is by no means restricted by these specific Examples.

Firstly, Examples for the preparation of the compounds of the present invention will be described.

Preparation Example 1

9-(4-Chlorophenylimino)-8-thia-1,6-diazabicyclo[4.3.0]nonane-7-one (Compound No. 12)

In a reaction flask, 3.2 g (13 mmol) of 1,2-tetramethylene-1-(4-chlorophenylthiocarbamoyl)-hydrazine, 2.2 g (28 mmol) of pyridine ad 20 ml of dichloromethane, were charged, and a dichloromethane solution containing 1.5 g (15 mmol) of phosgene was dropwise added while cooling the mixture with ice water. After the dropwise addition, the mixture was stirred at room temperature for 3 hours to complete the reaction. The reaction solution was washed with water, and dried over anhydrous sodium sulfate, and then the solvent was distilled off to obtain a crude product. This crude product was recrystallized from isopropyl ether to obtain 3.2 g (yield: 74%) of white crystals. Melting point: 82°–85° C.

Preparation Example 2

9-(4-Chlorophenylimino)-8-thia-1,6-diazabicyclo[4.3.0]nonane-7-thione (Compound No. 41)

Into a reaction flask, 2.4 g (9 mmol) of 1,2-tetramethylene-1-(4-chlorophenylthiocarbamoyl)-hydrazine, 2.0 g (25 mmol) of pyridine and 20 ml of dichloromethane, were charged, and 1.3 g (11 mmol) of thiophosgene was dropwise added while cooling the mixture with ice water. After the dropwise addition, the mixture was stirred at room temperature for 3 hours to complete the reaction. After the completion of the reaction, the reaction solution was washed with water, and dried over anhydrous sodium sulfate, and the solvent was distilled off to obtain a crude product. This crude product was recrystallized from isopropyl ether to obtain 2.1 g (yield:75%) of brown crystals. Melting point: 96°–97° C.

Preparation Example 3

9-(4-Chloro-3-hydroxyphenylimino)8-thia-1,6-diazabicyclo[4.3.0]nonane-7-one (Compound No. 46)

Into a reaction flask equipped with a Dimroth condenser, 1.7 g (5 mmol) of 9-(4-chloro-3-isopropoxyphenylimino)-8-thia-1,6-diazabicyclo[4.3.0]nonane-7-one, 1.3 g (10 mmol) of aluminum chloride and 50 ml of chloroform, were charged, and refluxed under heating for 2 hours to complete the reaction.

The reaction solution was poured into ice water, and the organic layer was washed with water and dried over anhydrous sodium sulfate, and the solvent was distilled off to obtain a crude product.

The crude product was purified by column chromatography to obtain 1.2 g (yield: 80%) of colorless crystals. Melting points: 130°–132° C.

Preparation Example 4

9-(4-Chloro-2-fluoro-3-propargyloxyphenylimino)-8-thia-1,6-diazabicyclo[4.3.0]nonane-7-one (Compound No. 35)

Into a reaction flask equipped with a Dimroth condenser, 2.2 g (7 mmol) of 9-(4-chloro-2-fluoro-3-hydroxyphenylimino)-8-thia-1,6-diazabicyclo[4.3.0]nonane-7-one, 1.1 g (9 mmol) of propargyl bromide, 1.3 g (9 mmol) of potassium carbonate and 20 ml of acetonitrile, were charged, and refluxed under heating for 3 hours to complete the reaction.

The reaction solution was filtered, concentrated, extracted with ethyl acetate, and then washed with water and dried over anhydrous sodium sulfate. The solvent was distilled off to obtain a crude product, which was then recrystallized from isopropyl ether to obtain 1.6 g (yield: 64%) of white crystals. Melting point: 132°–134° C.

Preparation Example 5

9-(4-Chloro-2-fluoro-5-ethoxycarbonylphenylimino)-8-thia-1,6-diazabicyclo[4.3.0]nonane-7-one (Compound No. 112)

Into a reaction flask, 3.8 g (11 mmol) of 1,2-tetramethylene-1-(4-chloro-2-fluoro-5-ethoxycarbonylphenylthiocarbamoyl)hydrazine, 2.1 g (26 mmol) of pyridine and 20 ml of dichloromethane, were charged, and a dichloromethane solution containaing 1.3 g (13 mmol) of phosgene, was dropwise added while cooling the mixture with ice water. After the dropwise addition, the mixture was stirred at room temperature for 1 hour to complete the reaction. The reaction solution was washed with water and dried over anhydrous sodium sulfate, and then the solvent was distilled off to obtain a crude product. This crude product was purified by column chromatography to obtain 2.8 g (yield: 68%) of colorless sticky substance. Refractive index: $n_D^{20}$ 1.6002.

Preparation Example 6

9-{4-Chloro-2-fluoro-5-(1-methoxyethoxycarbonylethoxy)phenylimino}-8-thia-1,6-diazabicyclo[4.3.0]nonane-7-one (Compound No. 128)

Into a reaction flask equipped with a Dimroth condenser, 1.9 g (6 mmol) of 9-(4-chloro-2-fluoro-3-hydroxyphenylimino)-8-thia-1,6-diazabicyclo[4.3.0]nonane-7-one, 1.3 g (6 mmol) of methoxyethyl 2-bromopropionate, 1.0 g (6 mmol) of potassium carbonate and 20 ml of acetonitrile, were charged, and refluxed under heating for 40 minutes to complete the reaction. The reaction solution was filtered, concentrated, extracted with ethyl ether, and then washed with water and dried over anhydrous sodium sulfate. The solvent was distilled off to obtian a crude product, which was purified by column chromatography to obtain 1.2 g (yield: 46.1%) of slightly brown liquid. Refractive index: $n_D^{20}$ 1.5749

Preparation Example 7

9-{4-Chloro-3-[1-(ethoxycarbonyl)ethylamino]-phenylimino}-8-thia-1,6-diazabicyclo[4.3.0]nonane-7-one (Compound No. 72)

Into a reaction flask equipped with a Dimroth condenser, 2.2 g (7.4 mmol) of 9-(4-chloro-3-aminophenylimino)-8-thia-1,6-diazabicyclo[4.3.0]nonane-7-one, 15 ml of ethyl 2-bromopropionate and 2.0 g (24 mmol) of sodium hydrogen carbonate, were charged, and refluxed under heating for 4 hours to complete the reaction. The reaction solution was filtered, concentrated and extracted with ethyl acetate, and then washed with water and dried over anhydrous sodium sulfate. The solvent was distilled off to obtain a crude product, which was purified by column chromatography to obtain 1.5 g (yield: 52%) of colorless oily substance. Refractive index: $n_D^{20}$ 1.5755

The 9-phenylimino-8-thia-1,6-diazabicyclo[4.3.0]nonane-7-(one or thione) derivative of the formula I is useful as an active ingredient for a herbicide. When the compound of the formula I of the present invention is used as a herbicide for a paddy rice field, an upland field, an orchard or a non-agricultural field, the active ingredient can be used in a suitable formulation depending upon the particular purpose. Usually, the active ingredient is diluted with an inert liquid or solid carrier, and used in the form of a formulation such as a dust, a wettable powder, an emulsifiable concentrate, a granule, etc., if necessary by adding a surfactant and other additives. Further, the compound of the present invention may be used in combination with an insecticide, a nematocide, a fungicide, other herbicides, a plant growth controlling agent, a fertilizer, etc., as the case requires.

Now, the formulations will be described in detail with reference to typical Formulation Examples. In the following Formulation Examples, "parts" means "parts by weight".

Formulation Example 1

Wettable powder 10.0 parts of Compound No. 43, 0.5 part of Emulgen (trademark of Kao Soap Co., Ltd.) 810, 0.5 part of Demol trademark of Kao Soap Co., Ltd.) N, 20.0 parts of Kunilite (trademark of Kunimine Kogyo K.K.) 201, and 69.0 parts of Zeeklite (trademark of Zeeklite Co., Ltd.) CA, were mixed and pulverized to obtain a wettable powder containing 10% of an active ingredient.

Formulation Example 2

Wettable powder 10.0 parts of Compound No. 33, 0.5 part of Emulgen 810, 0.5 part of Demol N, 20.0 parts of Kunilite 201, 5.0 parts of Carplex 80 and 64.0 parts of Zeeklite CA, were mixed and pulverized to obtain a wettable powder containing 10% of the active ingredient.

Formulation Example 3

Emulsifiable concentrate

To 30 parts of Compound No. 19, 60 parts of a mixture of xylene and isophorone in equal amounts and 10 parts of surfactant Sorpol (trademark of Toho Kagaku Kogyo K.K.) 800A, were added, and the mixture was thoroughly mixed to obtain 100 parts of an emulsifiable concentrate.

Formulation Example 4

Granules 10 parts of water was added to 10 parts of Compound No. 21, 80 parts of a filler obtained by mixing talc and bentonite in a ratio of 1:3, 5 parts of white carbon and 5 parts of surfactant Sorpol N 800A, and the mixture was thoroughly kneaded to obtain a paste, which was extruded from sieve openings having a diameter of 0.7 mm and dried, and then cut into a length of from 0.5 to 1 mm, to obtain 100 parts of granules.

The compounds of the formula of the present invention exhibit excellent herbicidal effects at a very low dose in a wide range from the germination stage to the growing stage of annual weeds such as barnyardgrass (*Echinochloa crus-galli*), umbrella-plant (*Cyperus difformis L.*), monochoria (*Monochoria vaginalis Presl*), spike-flowered rotala (*Rotala indica Koehne*), false pimpernel (*Lindernia procumbens Philcox*) and *Dopatrium junceum Hamilt*, and perennial weeds such as bulrush (*Scirpus juncoides Roxb.*), slender spikerush (*Eleocharis acicularis Roem. et Schult.*), water plantain (*Alisma canaliculatum A. Br. et Bouche*), Sagittaria (*Sagittaria pygmaea Miq.*) and cyperus sp. (*Cyperus serotinus Rottb.*) which grow in paddy fields. At the same time, they have high selectivity for paddy field rice. Further, they exhibit high herbicidal effects, by soil treatment or by foliage treatment, against various weeds in the upland fields, for example, broad leaf weeds such as smart weed (*Polygonum nodosum L.*), pigweed (*Amaranthus retroflexus*), lambsquaters (*Chenopodium album*), common chickweed (*Stellaria media*), speed well (*Veronica persica*), wild mustard (*Brassica kaber var. pinnatifida*) and cocklebur (*Xanthium strumarium*), cyperaceous weeds such as rice flatsedge (*Cyperus iria L.*), and gramineous weeds such as barnyardgrass, large crabgrass (*Digitaria sanguinalis*) and green foxtail (*Setaria viridis*). At the same time, they have a feature that they are highly safe to crop plants such as upland rice, wheat, soybean and corn.

The dose of the compound of the present invention is usually within a range of from 10 g to 15 kg/ha. More specifically, the dose is usually from 30 g to 5 kg/ha for upland fields, from 10 g to 1 kg/ha for paddy rice fields, and from 200 g to 5 kg/ha for non-agricultural fields.

Further, the compounds of the present invention have excellent residual effects, and show stabilized effects for a long period of time also in paddy fields. They are also useful for orchard, grassland, lawn and non-agricultural fields.

Now, the herbicidal effects of the herbicides of the present invention will be described with reference to Test Examples.

Test Example 1

Herbicidal test by soil treatment of paddy field

Into a 100 cm$^2$ porcelain pot, paddy field soil was filled and puddled. Then, seeds of barnyardgrass, umbrella plant, monochoria and bulrush were sown, and water was introduced to a depth of 3 cm.

Next day, the wettable powder prepared in accordance with Formulation Example 1, was diluted with water and dropwise applied to the surface of the water. The amount of the active ingredient applied, was 400 g/10a. Then, the pot was left in a green house. Twenty one days after the application, the herbicidal effects were evaluated in accordance with the standards identified in Table 3. The results are shown in Table 4.

TABLE 3

| Index | Herbicidal effects and phytotoxicity |
|---|---|
| 5 | Withered |
| 4.5 | Herbicidal effect (or phytotoxicity) in a range of 90 to 99% |
| 4 | Herbicidal effect (or phytotoxicity) in a range of 80 to 89% |
| 3.5 | Herbicidal effect (or phytotoxicity) in a range of 70 to 79% |
| 3 | Herbicidal effect (or phytotoxicity) in a range of 60 to 69% |
| 2.5 | Herbicidal effect (or phytotoxicity) in a range of 50 to 59% |
| 2 | Herbicidal effect (or phytotoxicity) in a range of 40 to 49% |
| 1.5 | Herbicidal effect (or phytotoxicity) in a range of 30 to 39% |
| 1 | Herbicidal effect (or phytotoxicity) in a range of 20 to 29% |
| 0.5 | Herbicidal effect (or phytotoxicity) in a range of 1 to 19% |
| 0 | No herbicidal effect (or no phytotoxicity) |

TABLE 4

| Compound No. | Herbicidal effects | | | |
|---|---|---|---|---|
| | Barnyard-grass | Umbrella plant | Monochoria | Bulrush |
| 1 | 4 | 5 | 5 | 4 |
| 2 | 2.5 | 2 | 5 | 3.5 |
| 3 | 4 | 5 | 5 | 2.5 |
| 4 | 4 | 4 | 5 | 4 |
| 6 | 4 | 5 | 5 | 3.5 |
| 7 | 5 | 5 | 5 | 4 |
| 8 | 3 | 4 | 5 | 5 |
| 9 | 5 | 5 | 5 | 5 |
| 10 | 5 | 5 | 5 | 5 |
| 11 | 5 | 5 | 5 | 5 |
| 12 | 5 | 5 | 5 | 5 |
| 13 | 5 | 5 | 5 | 5 |
| 14 | 5 | 5 | 5 | 5 |
| 15 | 4 | 4 | 5 | 5 |
| 16 | 5 | 5 | 5 | 5 |
| 17 | 5 | 5 | 5 | 5 |
| 18 | 5 | 5 | 5 | 5 |
| 19 | 5 | 5 | 5 | 5 |
| 20 | 5 | 5 | 5 | 5 |
| 21 | 5 | 5 | 5 | 5 |
| 22 | 5 | 5 | 5 | 5 |
| 23 | 5 | 5 | 5 | 5 |
| 24 | 5 | 5 | 5 | 5 |
| 25 | 5 | 5 | 5 | 5 |
| 26 | 5 | 5 | 5 | 5 |
| 27 | 5 | 5 | 5 | 5 |
| 28 | 5 | 5 | 5 | 5 |
| 29 | 5 | 5 | 5 | 5 |
| 30 | 5 | 5 | 5 | 5 |
| 31 | 5 | 5 | 5 | 5 |
| 32 | 5 | 5 | 5 | 5 |
| 33 | 5 | 5 | 5 | 5 |
| 34 | 5 | 5 | 5 | 5 |
| 35 | 5 | 5 | 5 | 5 |
| 36 | 5 | 5 | 5 | 5 |
| 37 | 5 | 5 | 5 | 5 |
| 38 | 5 | 5 | 5 | 5 |
| 39 | 5 | 5 | 5 | 5 |
| 40 | 5 | 5 | 5 | 5 |
| 41 | 5 | 5 | 5 | 5 |
| 42 | 5 | 5 | 5 | 5 |
| 43 | 5 | 5 | 5 | 5 |
| 44 | 5 | 5 | 5 | 5 |
| 45 | 5 | 5 | 5 | 5 |
| 46 | 5 | 5 | 5 | 5 |
| 47 | 5 | 5 | 5 | 5 |
| 48 | 5 | 5 | 5 | 5 |
| 49 | 5 | 5 | 5 | 5 |
| 50 | 5 | 5 | 5 | 5 |
| 51 | 5 | 5 | 5 | 5 |
| 52 | 5 | 5 | 5 | 5 |
| 53 | 5 | 5 | 5 | 5 |
| 54 | 5 | 5 | 5 | 5 |
| 55 | 5 | 5 | 5 | 5 |

Test Example 2

Low dose test in soil treatment of irrigated paddy field

Into a 1/5,000a Wagner pot, paddy field soil was filled and puddled, and water was introduced to a depth of 3 cm.

In pot A, three germinated tubers of each of flat sedge and sagittaria, were embedded in the surface layer of the soil, and two seedlings of two rice plants of 2.2 leaf stage, were transplanted in a depth of 2 cm.

In pot B, seeds of barnyardgrass, hardstem bulrush, narrow leaf water plantain, monochoria and umbrella plant were sown in the surface layer of the soil.

The day after the seeding and transplantation, a prescribed amount of a wettable powder of each compound formulated in accordance with Formulation Example 1, was diluted with water and dropwise applied by a pipette.

Thirty days after application, the herbicidal effect and phytotoxicity were evaluated in accordance with the standards identified in Table 3. The results are shown in Table 5.

TABLE 5

| Compound No. | Dose of active ingredient (g/10 a) | (Part 1) | | | | (Part 2) | | | |
|---|---|---|---|---|---|---|---|---|---|
| | | Barnyard-grass | Umbrella plant | Monochoria | Bulrush | Water plantain | Sagittaria | Cyperus sp | Transplanted paddy field rice |
| 13 | 50 | 5 | 5 | 5 | 4.5 | 5 | 5 | 5 | 0.5 |
| | 25 | 4.5 | 5 | 5 | 4 | 5 | 5 | 5 | 0 |
| 18 | 50 | 5 | 5 | 5 | 5 | 5 | 5 | 5 | 0 |
| | 25 | 5 | 5 | 5 | 5 | 5 | 5 | 5 | 0 |
| 19 | 12.5 | 5 | 5 | 5 | 5 | 5 | 5 | 5 | 0 |
| | 6.3 | 5 | 5 | 5 | 5 | 5 | 4.5 | 5 | 0 |
| 20 | 25 | 5 | 5 | 5 | 5 | 5 | 5 | 5 | 0 |
| | 12.5 | 5 | 5 | 5 | 5 | 5 | 5 | 5 | 0 |
| 21 | 25 | 5 | 5 | 5 | 5 | 5 | 5 | 5 | 0 |
| | 12.5 | 5 | 5 | 5 | 5 | 5 | 5 | 5 | 0 |
| 22 | 25 | 5 | 5 | 5 | 5 | 5 | 5 | 5 | 0 |
| | 12.5 | 5 | 5 | 5 | 5 | 5 | 5 | 5 | 0 |
| 23 | 25 | 5 | 5 | 5 | 5 | 5 | 5 | 5 | 0 |
| | 12.5 | 5 | 5 | 5 | 5 | 5 | 5 | 5 | 0 |
| 24 | 25 | 5 | 5 | 5 | 5 | 5 | 5 | 5 | 0 |
| | 12.5 | 5 | 5 | 5 | 5 | 5 | 4 | 5 | 0 |
| 26 | 25 | 5 | 5 | 5 | 5 | 5 | 4 | 5 | 1 |
| | 12.5 | 5 | 5 | 5 | 5 | 5 | 2 | 5 | 0 |
| 30 | 50 | 5 | 5 | 5 | 5 | 5 | 5 | 5 | 0.5 |
| | 25 | 5 | 5 | 5 | 5 | 5 | 5 | 5 | 0 |
| 31 | 50 | 5 | 5 | 5 | 5 | 5 | 5 | 5 | 0 |
| | 25 | 5 | 5 | 5 | 5 | 5 | 5 | 5 | 0 |
| 32 | 6.3 | 5 | 5 | 5 | 5 | 5 | 5 | 5 | 1 |
| | 3.2 | 5 | 5 | 5 | 5 | 5 | 5 | 5 | 0.5 |
| 33 | 6.3 | 5 | 5 | 5 | 5 | 5 | 5 | 5 | 0.5 |
| | 3.2 | 5 | 5 | 5 | 5 | 5 | 5 | 5 | 0 |
| 34 | 6.3 | 5 | 5 | 5 | 5 | 5 | 5 | 5 | 1 |
| | 3.2 | 5 | 5 | 5 | 5 | 5 | 5 | 5 | 0.5 |
| 35 | 6.3 | 5 | 5 | 5 | 5 | 5 | 5 | 5 | 3.5 |

TABLE 5-continued

| Compound No. | Dose of active ingredient (g/10 a) | (Part 1) Barnyard-grass | Umbrella plant | Monochoria | Bulrush | (Part 2) Water plantain | Sagittaria | Cyperus sp | Transplanted paddy field rice |
| --- | --- | --- | --- | --- | --- | --- | --- | --- | --- |
|  | 3.2 | 5 | 5 | 5 | 5 | 5 | 5 | 5 | 3 |
| 36 | 12.5 | 5 | 5 | 5 | 5 | 5 | 5 | 4 | 2 |
|  | 6.3 | 5 | 5 | 5 | 4 | 5 | 5 | 2 | 1 |
| 37 | 25 | 5 | 5 | 5 | 5 | 5 | 5 | 5 | 0 |
|  | 12.5 | 5 | 5 | 5 | 5 | 5 | 5 | 5 | 0 |
| 38 | 25 | 5 | 5 | 5 | 5 | 5 | 5 | 5 | 0 |
|  | 12.5 | 5 | 5 | 5 | 5 | 5 | 5 | 5 | 0 |
| 39 | 25 | 5 | 5 | 5 | 5 | 5 | 5 | 5 | 1 |
|  | 12.5 | 5 | 5 | 5 | 3.5 | 5 | 5 | 2 | 0 |
| 42 | 25 | 5 | 5 | 5 | 5 | 5 | 5 | 5 | 0 |
|  | 12.5 | 5 | 5 | 5 | 5 | 5 | 5 | 5 | 0 |
| 43 | 12.5 | 5 | 5 | 5 | 5 | 5 | 5 | 5 | 0 |
|  | 6.3 | 5 | 5 | 5 | 5 | 5 | 5 | 5 | 0 |
| Ronstar | 50 | 5 | 5 | 5 | 5 | 5 | 4.5 | 5 | 2 |
|  | 25 | 5 | 5 | 5 | 5 | 5 | 2.5 | 5 | 2 |
|  | 12.5 | 5 | 5 | 5 | 5 | 5 | 1.5 | 3 | 1 |

Test Example 3

The herbicidal test in soil treatment of upland field

Into a 120 cm² plastic pot, upland field soil was filled, and seeds of barnyardgrass, large crabgrass, smart weed, pigweed, lambsquaters and rice flatsedge were sown and covered with soil.

A wettable powder of each test compound formulated in accordance with Formulation Example 1, was diluted with water in an amount of 100 liter/10a and uniformly applied to the surface of soil by means of a small size spray at a dose of 400 g/10a of the active ingredient. After the application, the pot was left for 21 days in a green house, and then the herbicidal effects were evaluated in accordance with the standards identified in Table 3. The results are shown in Table 6.

TABLE 6

| Compound No. | Herbicidal effects Barnyard-grass | Large crabgrass | Smart weed | Pig-weed | Lambs-quaters | Rice flatsedge |
| --- | --- | --- | --- | --- | --- | --- |
| 4 | 4 | 5 | 5 | 5 | 5 | 5 |
| 11 | 5 | 5 | 5 | 5 | 5 | 5 |
| 12 | 5 | 5 | 5 | 5 | 5 | 5 |
| 16 | 5 | 5 | 5 | 5 | 5 | 5 |
| 17 | 5 | 5 | 5 | 5 | 5 | 5 |
| 20 | 5 | 5 | 5 | 5 | 5 | 5 |
| 22 | 4 | 5 | 5 | 5 | 5 | 5 |
| 23 | 4 | 5 | 5 | 5 | 5 | 5 |
| 24 | 5 | 5 | 5 | 5 | 5 | 5 |
| 28 | 5 | 5 | 4 | 5 | 5 | 5 |
| 31 | 5 | 5 | 5 | 5 | 5 | 5 |
| 33 | 5 | 5 | 5 | 5 | 5 | 5 |
| 34 | 5 | 5 | 5 | 5 | 5 | 5 |
| 35 | 5 | 5 | 5 | 5 | 5 | 5 |
| 36 | 5 | 5 | 5 | 5 | 5 | 5 |

Test Example 4

The herbicidal test in foliage treatment in upland field

Into a 120 cm² plastic pot, upland field soil was filled, and seeds of barnyardgrass, large crabgrass, smart weed, pigweed, lambsquater and rice flatsedge, were sown, and grown in a green house until barnyardgrass grew to the 3 leaf stage. When barnyardgrass reached the 3 leaf stage, a wettable powder of each test compound formulated in accordance with Formulation Example 1 was diluted with water in an amount of 100 liter/10 a and applied to the foliage of the plants from above by a small size spray at a dose of 400 g/10 a of the active ingredient. After the application, the pot was left for 21 days in a green house, and then the herbicidal effects were evaluated in accordance with the standards identified in Table 3. The results are shown in Table 7.

TABLE 7

| Compound No. | Herbicidal effects Barnyard-grass | Large crabgrass | Smart weed | Pig-weed | Lambs-quaters | Rice flatsedge |
| --- | --- | --- | --- | --- | --- | --- |
| 7 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 16 | 5 | 5 | 5 | 5 | 5 | 5 |
| 17 | 5 | 5 | 5 | 5 | 5 | 5 |
| 20 | 5 | 5 | 5 | 5 | 5 | 5 |
| 21 | 4 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 28 | 5 | 5 | 5 | 5 | 5 | 5 |
| 31 | 4 | 5 | 5 | 5 | 5 | 5 |
| 32 | 4 | 5 | 5 | 5 | 5 | 5 |
| 33 | 5 | 5 | 5 | 5 | 5 | 5 |
| 34 | 5 | 5 | 5 | 5 | 5 | 5 |
| 35 | 5 | 5 | 5 | 5 | 5 | 5 |
| 36 | 5 | 5 | 5 | 5 | 5 | 5 |
| 37 | 5 | 5 | 5 | 5 | 5 | 5 |
| 38 | 4 | 5 | 5 | 5 | 5 | 5 |
| 39 | 5 | 5 | 5 | 5 | 5 | 5 |
| 41 | 4 | 5 | 5 | 5 | 5 | 5 |
| 42 | 4 | 5 | 5 | 5 | 5 | 5 |
| 43 | 5 | 5 | 5 | 5 | 5 | 5 |
| 44 | 4 | 5 | 5 | 5 | 5 | 5 |

Test Example 5

Herbicidal test in the soil treatment of paddy rice field

Into a 10 cm² porcelain pot, paddy field soil was filled and puddled, and seeds of barnyardgrass, umbrella plant, monochoria and bulrush were sown. Then, water was introduced to the depth of 3 cm.

Next day, a wettable powder prepared in accordance with Formulation Example 1, was diluted with water and dropwise applied to the surface of water. The amount of the active ingredient applied was 400 g/10a. The pot was left in a green house, and twenty one days after the application, the herbicidal activities were evaluated in accordance with the standards identified in Table 3. The results are shown in Table 8.

TABLE 8

| Compound No. | Herbicidal effects | | | |
|---|---|---|---|---|
| | Barnyardgrass | Umbrella plant | Monochoria | Bulrush |
| 56 | 5 | 5 | 5 | 5 |
| 57 | 5 | 5 | 5 | 5 |
| 58 | 5 | 5 | 5 | 5 |
| 59 | 5 | 5 | 5 | 5 |
| 60 | 5 | 5 | 5 | 5 |
| 61 | 5 | 5 | 5 | 5 |
| 62 | 5 | 5 | 5 | 5 |
| 63 | 5 | 5 | 5 | 5 |
| 64 | 5 | 5 | 5 | 5 |
| 65 | 5 | 5 | 5 | 5 |
| 66 | 5 | 5 | 5 | 5 |
| 67 | 5 | 5 | 5 | 5 |
| 68 | 5 | 5 | 5 | 5 |
| 69 | 5 | 5 | 5 | 5 |
| 70 | 5 | 5 | 5 | 5 |
| 71 | 5 | 5 | 5 | 5 |
| 72 | 5 | 5 | 5 | 5 |
| 73 | 5 | 5 | 5 | 5 |
| 74 | 5 | 5 | 5 | 5 |
| 75 | 5 | 5 | 5 | 5 |
| 76 | 5 | 5 | 5 | 5 |
| 77 | 5 | 5 | 5 | 5 |
| 78 | 5 | 5 | 5 | 5 |
| 79 | 5 | 5 | 5 | 5 |
| 80 | 5 | 5 | 5 | 5 |
| 81 | 5 | 5 | 5 | 5 |
| 82 | 5 | 5 | 5 | 5 |
| 84 | 5 | 5 | 5 | 5 |
| 85 | 5 | 5 | 5 | 5 |
| 86 | 5 | 5 | 5 | 5 |
| 87 | 5 | 5 | 5 | 5 |
| 88 | 5 | 5 | 5 | 5 |
| 89 | 5 | 5 | 5 | 5 |
| 90 | 5 | 5 | 5 | 5 |
| 92 | 5 | 5 | 5 | 5 |
| 93 | 5 | 5 | 5 | 5 |
| 94 | 5 | 5 | 5 | 5 |
| 95 | 5 | 5 | 5 | 5 |
| 96 | 5 | 5 | 5 | 5 |
| 97 | 5 | 5 | 5 | 5 |
| 98 | 5 | 5 | 5 | 5 |
| 99 | 5 | 5 | 5 | 5 |
| 100 | 5 | 5 | 5 | 5 |
| 102 | 5 | 5 | 5 | 5 |
| 103 | 5 | 5 | 5 | 5 |
| 104 | 5 | 5 | 5 | 5 |
| 105 | 5 | 5 | 5 | 5 |
| 106 | 5 | 5 | 5 | 5 |
| 107 | 5 | 5 | 5 | 5 |
| 108 | 5 | 5 | 5 | 5 |
| 109 | 5 | 5 | 5 | 5 |
| 110 | 5 | 5 | 5 | 5 |
| 111 | 5 | 5 | 5 | 5 |
| 112 | 5 | 5 | 5 | 5 |
| 113 | 5 | 5 | 5 | 5 |
| 114 | 5 | 5 | 5 | 5 |
| 115 | 5 | 5 | 5 | 5 |
| 122 | 5 | 5 | 5 | 5 |
| 123 | 5 | 5 | 5 | 5 |
| 124 | 5 | 5 | 5 | 5 |
| 125 | 5 | 5 | 5 | 5 |
| 126 | 5 | 5 | 5 | 5 |
| 127 | 5 | 5 | 5 | 5 |
| 128 | 5 | 5 | 5 | 5 |
| 129 | 5 | 5 | 5 | 5 |
| 130 | 5 | 5 | 5 | 5 |
| 131 | 5 | 5 | 5 | 5 |
| 132 | 5 | 5 | 5 | 5 |
| 133 | 5 | 5 | 5 | 5 |
| 136 | 5 | 5 | 5 | 5 |
| 137 | 5 | 5 | 5 | 5 |
| 138 | 5 | 5 | 5 | 5 |
| 139 | 5 | 5 | 5 | 5 |
| 140 | 5 | 5 | 5 | 5 |
| 141 | 5 | 5 | 5 | 5 |
| 142 | 5 | 5 | 5 | 5 |
| 143 | 5 | 5 | 5 | 5 |
| 144 | 5 | 5 | 5 | 5 |

Test Example 6

Low dose test in the soil treatment of irrigated paddy rice field

Into a 1/5,000a Wagner pot, paddy field soil was filled and puddled, and then water was introduced to a depth of 3 cm.

In pot A, three germinated tubers of each of water nutgrass and sagittaria, were embedded in the surface layer of the soil, and two seedlings of two paddy field rice plants of 2.2 leaf stage, were transplanted in a depth of 2 cm.

In pot B, seeds of barnyardgrass, bulrush, water plantain, monochoria and umbrella plant, were sown in the surface layer of the soil.

The day after the seeding and transplantation, a prescribed amount of a wettable powder of each compound formulated in accordance with Formulation Example 1, was diluted with water and dropwise applied by a pippet.

Thirty days after the application, the herbicidal effects were evaluated in accordance with the standards identified in Table 3. The results are shown in Table 9.

TABLE 9

| Compound No. | Dose of active ingredient (g/10 a) | Barnyard-grass | Umbrella plant | Monochoria | Bulrush | Water plantain | Sagittaria | Flat sedge | Transplanted paddy field rice |
|---|---|---|---|---|---|---|---|---|---|
| 57 | 25 | 5 | 5 | 5 | 5 | 5 | 5 | 5 | 0 |
| | 12.5 | 5 | 5 | 5 | 5 | 5 | 5 | 5 | 0 |
| 58 | 25 | 5 | 5 | 5 | 5 | 5 | 5 | 5 | 0 |
| | 12.5 | 5 | 5 | 5 | 5 | 5 | 5 | 5 | 0 |
| 59 | 25 | 5 | 5 | 5 | 5 | 5 | 5 | 5 | 1 |
| 60 | 12.5 | 5 | 5 | 5 | 5 | 5 | 5 | 5 | 1 |
| | 6.3 | 5 | 5 | 5 | 5 | 5 | 5 | 5 | 0 |
| 61 | 50 | 5 | 5 | 5 | 5 | 5 | 5 | 5 | 0 |
| | 25 | 5 | 5 | 5 | 5 | 5 | 5 | 5 | 0 |
| 63 | 25 | 5 | 5 | 5 | 5 | 5 | 5 | 5 | 0 |
| | 12.5 | 5 | 5 | 5 | 5 | 5 | 5 | 5 | 0 |
| 64 | 25 | 5 | 5 | 5 | 5 | 5 | 5 | 5 | 0 |
| | 12.5 | 5 | 5 | 5 | 5 | 5 | 5 | 5 | 0 |
| 67 | 6.3 | 5 | 5 | 5 | 5 | 5 | 5 | 5 | 1 |
| 68 | 50 | 5 | 5 | 5 | 5 | 5 | 5 | 5 | 0 |
| | 25 | 5 | 5 | 5 | 5 | 5 | 4 | 5 | 0 |
| 69 | 50 | 5 | 5 | 5 | 5 | 5 | 5 | 4 | 0 |

TABLE 9-continued

| Compound No. | Dose of active ingredient (g/10 a) | Barnyard-grass | Umbrella plant | Monochoria | Bulrush | Water plantain | Sagittaria | Flat sedge | Transplanted paddy field rice |
|---|---|---|---|---|---|---|---|---|---|
| | 25 | 5 | 5 | 5 | 5 | 5 | 5 | 4 | 0 |
| 72 | 50 | 5 | 5 | 5 | 5 | 5 | 5 | 5 | 1 |
| 73 | 50 | 5 | 5 | 5 | 5 | 5 | 5 | 3 | 0 |
| 76 | 25 | 5 | 5 | 5 | 5 | 5 | 5 | 5 | 0 |
| | 12.5 | 5 | 5 | 5 | 5 | 5 | 5 | 5 | 0 |
| 77 | 25 | 5 | 5 | 5 | 5 | 5 | 5 | 5 | 0 |
| | 12.5 | 5 | 5 | 5 | 5 | 5 | 5 | 5 | 0 |
| 79 | 50 | 5 | 5 | 5 | 5 | 5 | 5 | 5 | 0 |
| | 25 | 5 | 5 | 5 | 5 | 5 | 5 | 5 | 0 |
| 81 | 50 | 5 | 5 | 5 | 5 | 5 | 5 | 5 | 0.5 |
| | 25 | 5 | 5 | 5 | 5 | 5 | 5 | 5 | 0.5 |
| 94 | 25 | 5 | 5 | 5 | 5 | 5 | 5 | 5 | 1 |
| | 12.5 | 5 | 5 | 5 | 5 | 5 | 4 | 4 | 1 |
| 95 | 50 | 5 | 5 | 5 | 5 | 5 | 5 | 5 | 2 |
| | 25 | 5 | 5 | 5 | 5 | 5 | 5 | 5 | 1 |
| 98 | 50 | 5 | 5 | 5 | 5 | 5 | 5 | 5 | 0 |
| 103 | 50 | 5 | 5 | 5 | 5 | 5 | 5 | 4 | 1 |
| 122 | 25 | 5 | 5 | 5 | 5 | 5 | 5 | 5 | 0 |
| | 12.5 | 5 | 5 | 5 | 5 | 5 | 5 | 5 | 0 |
| 123 | 50 | 5 | 5 | 5 | 5 | 5 | 5 | 5 | 0 |
| | 25 | 5 | 5 | 5 | 5 | 5 | 5 | 5 | 0 |
| 124 | 50 | 5 | 5 | 5 | 5 | 5 | 5 | 5 | 1 |
| | 25 | 5 | 5 | 5 | 5 | 5 | 5 | 5 | 0 |
| 141 | 6.3 | 5 | 4 | 5 | 5 | 5 | 5 | 5 | 1 |
| 143 | 50 | 5 | 5 | 5 | 5 | 5 | 5 | 5 | 0 |
| | 25 | 5 | 5 | 5 | 5 | 5 | 5 | 5 | 0 |
| 144 | 50 | 5 | 5 | 5 | 5 | 5 | 5 | 5 | 2 |
| | 25 | 5 | 5 | 5 | 5 | 5 | 5 | 5 | 1 |
| Ronstar | 50 | 5 | 5 | 5 | 5 | 5 | 5 | 5 | 2 |
| | 25 | 5 | 5 | 5 | 5 | 5 | 2 | 5 | 2 |
| | 12.5 | 5 | 5 | 5 | 5 | 5 | 1 | 2 | 1 |

Test Example 7

Herbicidal test in the soil treatment of upland field

Into a 120 cm² plastic pot, upland field soil was filled and seeds of barnyardgrass, large crabgrass, smart weed, pigweed, lambsquater and rice flatsedge were sown and covered with soil. A wettable powder of each test compound formulated in accordance with Formulation Example 1, was diluted with water in an amount of 100 liter/10a and uniformly applied to the surface of the soil by a small size spray at a dose of 400 g/10a of the active ingredient. After the treatment, the pot was left in a green house for 21 days, and then the herbicidal effects were evaluated in accordance with the standards identified in Table 3. The results are shown in Table 10.

TABLE 10

| Compound No. | Barnyard-grass | Large crabgrass | Smart weed | Pig-weed | Lambs-quaters | Rice flatsedge |
|---|---|---|---|---|---|---|
| 58 | 4 | 5 | 5 | 5 | 5 | 5 |
| 59 | 4 | 5 | 5 | 5 | 5 | 5 |
| 63 | 3 | 5 | 5 | 5 | 5 | 5 |
| 64 | 3 | 5 | 5 | 5 | 5 | 5 |
| 67 | 5 | 5 | 5 | 5 | 5 | 5 |
| 71 | 3 | 5 | 5 | 5 | 5 | 5 |
| 76 | 3 | 5 | 5 | 5 | 5 | 5 |
| 81 | 4 | 5 | 5 | 5 | 5 | 5 |
| 95 | 5 | 5 | 4 | 5 | 5 | 5 |
| 103 | 3 | 5 | 5 | 5 | 5 | 5 |
| 107 | 3 | 5 | 5 | 5 | 5 | 5 |
| 108 | 3 | 5 | 5 | 5 | 5 | 5 |
| 112 | 5 | 5 | 5 | 5 | 5 | 5 |
| 113 | 3 | 5 | 5 | 5 | 5 | 5 |
| 114 | 4 | 5 | 5 | 5 | 5 | 5 |
| 123 | 3 | 5 | 5 | 5 | 5 | 5 |
| 128 | 5 | 5 | 5 | 5 | 5 | 5 |
| 129 | 5 | 5 | 4 | 5 | 5 | 5 |
| 130 | 5 | 5 | 5 | 5 | 5 | 5 |
| 133 | 5 | 5 | 5 | 5 | 5 | 5 |
| 141 | 5 | 5 | 5 | 5 | 5 | 5 |
| 142 | 4 | 5 | 5 | 5 | 5 | 5 |

Test Example 8

Herbicidal test in the foliage treatment of upland field

Into a 120 cm² plastic pot, upland field soil was filled, and seeds of barnyardgrass, large crabgrass, smart weed, pigweed, lambsquater and rice flatsedge, were sown, and grown in a green house until barnyardgrass grew to the 3 leaf stage. When barnyardgrass reached the 3 leaf stage, a wettable powder of each test compound prepared in accordance with Formulation Example 1 was diluted with water in an amount of 100 liter/10a and applied to the foliage of the plants from above by a small size spray at a dose of 400 g/10a of the active ingredient. After the application, the pot was left in a green house for 21 days, and then the herbicidal effects were evaluated in accordance with the standards identified in Table 3. The results are shown in Table 11.

TABLE 11

| Compound No. | Barnyard-grass | Large crabgrass | Smart weed | Pig-weed | Lambs-quaters | Rice flatsedge |
|---|---|---|---|---|---|---|
| 57 | 4 | 5 | 5 | 5 | 5 | 5 |
| 58 | 5 | 5 | 5 | 5 | 5 | 5 |
| 59 | 5 | 5 | 5 | 5 | 5 | 5 |
| 60 | 4 | 5 | 5 | 5 | 5 | 5 |
| 61 | 5 | 5 | 5 | 5 | 5 | 5 |

TABLE 11-continued

| Compound No. | Herbicidal effects | | | | | |
|---|---|---|---|---|---|---|
| | Barnyard-grass | Large crabgrass | Smart weed | Pig-weed | Lambs-quarters | Rice flatsedge |
| 63 | 5 | 5 | 5 | 5 | 5 | 5 |
| 64 | 5 | 5 | 5 | 5 | 5 | 5 |
| 67 | 5 | 5 | 5 | 5 | 5 | 5 |
| 68 | 5 | 4 | 5 | 5 | 5 | 5 |
| 69 | 5 | 5 | 5 | 5 | 5 | 5 |
| 70 | 5 | 5 | 5 | 5 | 5 | 5 |
| 71 | 5 | 5 | 5 | 5 | 5 | 5 |
| 72 | 5 | 5 | 5 | 5 | 5 | 5 |
| 73 | 4 | 4 | 5 | 5 | 5 | 5 |
| 76 | 4 | 5 | 5 | 5 | 5 | 5 |
| 77 | 4 | 4 | 5 | 5 | 5 | 5 |
| 80 | 4 | 4 | 5 | 5 | 5 | 5 |
| 81 | 5 | 5 | 5 | 5 | 5 | 5 |
| 84 | 5 | 5 | 5 | 5 | 5 | 5 |
| 85 | 5 | 5 | 5 | 5 | 5 | 5 |
| 86 | 5 | 5 | 5 | 5 | 5 | 5 |
| 87 | 5 | 5 | 5 | 5 | 5 | 5 |
| 88 | 3 | 3 | 5 | 5 | 5 | 5 |
| 89 | 3 | 4 | 5 | 5 | 5 | 5 |
| 92 | 5 | 4 | 5 | 5 | 5 | 5 |
| 93 | 5 | 5 | 5 | 5 | 5 | 5 |
| 94 | 4 | 5 | 5 | 5 | 5 | 5 |
| 95 | 5 | 5 | 5 | 5 | 5 | 5 |
| 97 | 5 | 5 | 5 | 5 | 5 | 5 |
| 98 | 5 | 5 | 5 | 5 | 5 | 5 |
| 99 | 4 | 5 | 5 | 5 | 5 | 5 |
| 102 | 4 | 4 | 5 | 5 | 5 | 5 |
| 103 | 5 | 5 | 5 | 5 | 5 | 5 |
| 104 | 4 | 5 | 5 | 5 | 5 | 5 |
| 105 | 4 | 5 | 5 | 5 | 5 | 5 |
| 106 | 4 | 4 | 5 | 5 | 5 | 5 |
| 107 | 5 | 5 | 5 | 5 | 5 | 5 |
| 108 | 5 | 5 | 5 | 5 | 5 | 5 |
| 109 | 5 | 5 | 5 | 5 | 5 | 5 |
| 110 | 5 | 5 | 5 | 5 | 5 | 5 |
| 111 | 4 | 5 | 5 | 5 | 5 | 5 |
| 112 | 5 | 5 | 5 | 5 | 5 | 5 |
| 113 | 5 | 5 | 5 | 5 | 5 | 5 |
| 114 | 5 | 5 | 5 | 5 | 5 | 5 |
| 123 | 5 | 5 | 5 | 5 | 5 | 5 |
| 123 | 5 | 5 | 5 | 5 | 5 | 5 |
| 125 | 5 | 5 | 5 | 5 | 5 | 5 |
| 126 | 5 | 5 | 5 | 5 | 5 | 5 |
| 127 | 5 | 5 | 5 | 5 | 5 | 5 |
| 128 | 5 | 5 | 5 | 5 | 5 | 5 |
| 129 | 5 | 5 | 5 | 5 | 5 | 5 |
| 130 | 5 | 5 | 5 | 5 | 5 | 5 |
| 132 | 5 | 5 | 5 | 5 | 5 | 5 |
| 133 | 5 | 5 | 5 | 5 | 5 | 5 |
| 136 | 5 | 4 | 5 | 5 | 5 | 5 |
| 139 | 4 | 5 | 5 | 5 | 5 | 5 |
| 141 | 5 | 5 | 5 | 5 | 5 | 5 |
| 142 | 5 | 5 | 5 | 5 | 5 | 5 |
| 144 | 4 | 5 | 5 | 5 | 5 | 5 |

We claim:
1. A 9-phenylimino-8-thia-1,6-diazabicyclo[4.3.0]nonane-7-(one or thione) compound having the formula:

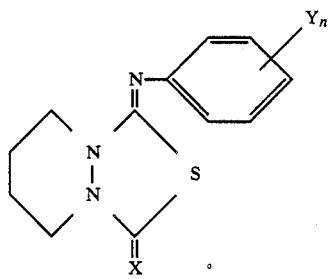

wherein Y which may be the same or different, represents chlorine, bromine, fluorine, hydroxyl, lower alkyl, lower alkoxy which may be substituted by chlorine, bromine or fluorine, lower alkenyloxy which may be substituted by chlorine, bromine or fluorine, lower alkynyloxy, phenoxy, lower cycloalkyloxy, lower alkoxycarbonyl-lower alkenyloxy, lower alkylthiocarbonyl-lower alkyloxy, lower alkynyloxycarbonyl-lower alkyloxy, benzyloxycarbonyl-lower alkyloxy, trifluoromethyl, benzyloxy which may be substituted by chlorine or lower alkyl, lower alkenyl, cyano-lower alkyl, lower alkylcarbamoyloxy, benzyl which may be substituted by one or two lower alkyl, lower alkoxy-lower alkyl, lower alkynyloxy-lower alkyl, lower cycloalkyl-methyloxy which may be substituted by chlorine, bromine or fluorine, lower alkoxy-lower alkyloxy, phenethyloxy, lower cycloalkyloxycarbonyl-lower alkyloxy, pyrrolidinocarbonyl, phenylcarbonyl which may be substituted by lower alkyl,

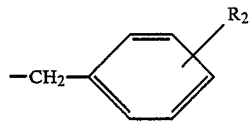

wherein $R_1$ is hydrogen, lower alkyl, phenyl, lower cycloalkyl, lower alkoxy-lower alkyl, lower alkoxycarbonyl-lower alkyl or

(wherein $R_2$ is hydrogen or lower alkoxy), X is oxygen or sulfur,

(wherein $R_3$ is lower alkyl, lower alkenyl or lower alkynyl, and m is 0 or 2),

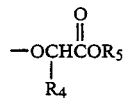

wherein $R_4$ is hydrogen or lower alkyl, and $R_5$ is hydrogen, lower alkyl, lower alkoxy-lower alkyl, tetrahydrofurfuryl, lower alkoxy-lower alkyloxy-lower alkyl, lower alkoxycarbonyl-lower alkyl or $N=C(CH_3)-R_6$ (wherein $R_6$ is lower alkyl or phenyl), $-NHR_7$ (wherein $R_7$ is lower alkylcarbonyl or lower alkoxycarbonyl-lower alkyl),

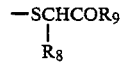

(wherein $R_8$ is hydrogen or lower alkyl, and $R_9$ is lower alkoxy, lower cycloalkyloxy or pyrrolidinyl), or

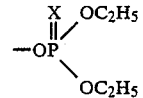

(wherein X is as defined above); n is an integer or from 0 to 3; and X is oxygen or sulfur.

2. The compound according to claim 1, wherein Y is chlorine, bromine or fluorine, lower alkoxy which may be substituted by chlorine, bromine or fluorine, lower alkenyloxy which may be substituted by chlorine, bromine or fluorine, lower alkynyloxy, phenoxy, benxyloxy which may be substituted by chlorine or lower alkyl,

wherein $R_1$ is hydrogen, lower alkyl, phenyl, lower cycloalkyl, lower alkoxy-lower alkyl, lower alkoxycarbonyl-lower alkyl or

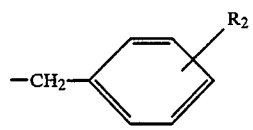

(wherein $R_2$ is hydrogen or lower alkoxy), X is oxygen or sulfur,

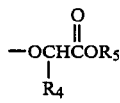

wherein $R_4$ is hydrogen or lower alkyl, and $R_5$ is hydrogen, lower alkyl, lower alkynyl, benzyl, lower alkoxy-lower alkyl, tetrahydrofurfuryl, lower alkoxy-lower alkyloxy-lower alkyl, lower alkoxycarbonyl-lower alkyl, lower cycloalkyl, or $-N=C(CH_3)R_6$ (wherein $R_6$ is lower alkyl or phenyl).

3. The compound according to claim 1, which has the formula:

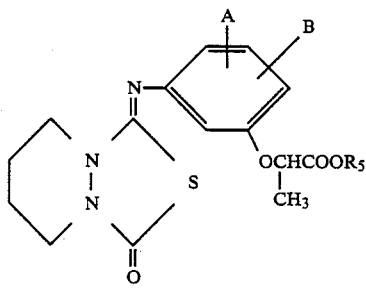

wherein A is hydrogen, chlorine, bromine or fluorine, B is chlorine, bromine or fluorine, and $R_5$ is hydrogen, lower alkyl, lower alkynyl, benzyl, lower alkoxy-lower alkyl, tetrahydrofurfuryl, lower alkoxy-lower alkyloxy-lower alkyl, lower alkoxycarbonyl-lower alkyl, lower cycloalkyl, or $-N=C(CH_3)R_6$ (wherein $R_6$ is lower alkyl or phenyl).

4. The compound according to claim 1, which has the formula:

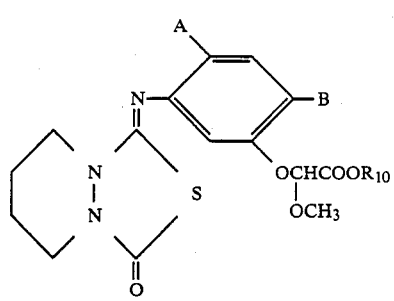

wherein A is hydrogen, chlorine, bromine or fluorine, B is chlorine, bromine or fluorine, and $R_{10}$ is hydrogen, lower alkyl, lower alkynyl, lower alkoxy-lower alkyl, lower alkoxy-lower alkyloxy-lower alkyl, or tetrahydrofurfuryl.

5. The compound according to claim 1, which has the formula:

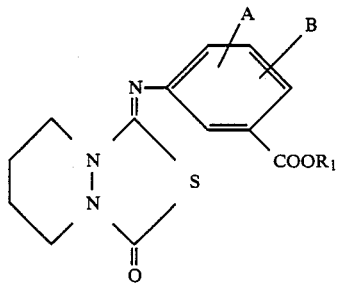

wherein A is hydrogen, chlorine, bromine or fluorine, B is chlorine, bromine or fluorine, and $R_1$ is hydrogen, lower alkyl, phenyl, lower cycloalkyl, lower alkoxy-lower alkyl, lower alkoxycarbonyl-lower alkyl or

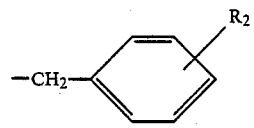

(wherein $R_2$ is hydrogen or lower alkoxy).

6. The compound according to claim 1, which has the formula:

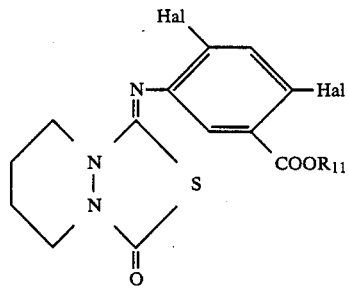

wherein Hal is chlorine, bromine or fluorine, and $R_{11}$ is hydrogen or lower alkyl.

7. A herbicidal composition comprising a herbicidally effective amount of a compound of the formula I as defined in claim 1 and a carrier.

8. A 9-phenylimino-8-thia-1,6-diazabicyclo[4.3.0]nonane-7-(one or thione) compound having the formula:

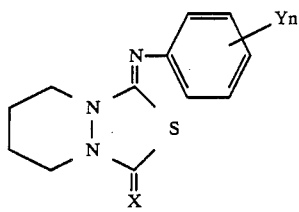

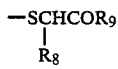

wherein Y is at least one halogen and a group represented by the formula:

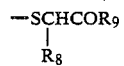

wherein $R_8$ is hydrogen or lower alkyl, and $R_9$ is lower alkoxy, lower cycloalkyloxy or pyrrolidinyl; X is oxygen or sulfur, and n is an integer from 2 to 3.

9. The compound according to claim 8, wherein $R_9$ is lower alkoxy.

10. The compound according to claim 8, wherein n is 3 having two chlorine or fluorine radicals and one radical of the formula $$-\underset{\underset{R_8}{|}}{S}CHCOR_9$$

wherein $R_8$ is hydrogen or lower alkyl, and $R_9$ is lower alkoxy, lower cycloalkoxy or pyrrolidinyl.

11. The compound according to claim 9, wherein n is an integer from 2 to 3.

12. The compound according to claim 11, wherein n is 3 having two chlorine or fluorine radicals and one radical of the formula:

$$-\underset{\underset{R_8}{|}}{S}CHCOR_9$$

wherein $R_8$ is hydrogen or lower alkyl, and $R_9$ is lower alkoxy, lower cycloalkoxy or pyrrolidinyl.

* * * * *